US008865184B2

(12) United States Patent
Ella et al.

(10) Patent No.: US 8,865,184 B2
(45) Date of Patent: Oct. 21, 2014

(54) VACCINE FOR CHIKUNGUNYA VIRUS INFECTION

(75) Inventors: Murthy Krishna Ella, Hyderabad (IN); Kandaswamy Sumathy, Hyderabad (IN); Jaya Sheela Pydigummala, Hyderabad (IN); Nagendra R. Hegde, Hyderabad (IN)

(73) Assignee: Bharat Biotech International Limited (IN)

( * ) Notice: Subject to any disclaimer, the term of this patent is extended or adjusted under 35 U.S.C. 154(b) by 1538 days.

(21) Appl. No.: 12/439,509

(22) PCT Filed: Aug. 31, 2007

(86) PCT No.: PCT/IN2007/000383
§ 371 (c)(1),
(2), (4) Date: Feb. 27, 2009

(87) PCT Pub. No.: WO2008/026225
PCT Pub. Date: Mar. 6, 2008

(65) Prior Publication Data
US 2013/0022631 A1   Jan. 24, 2013

(30) Foreign Application Priority Data
Sep. 1, 2006   (IN) .......................... 1583/CHE/2006

(51) Int. Cl.
*A61K 39/12*   (2006.01)
*A61K 39/00*   (2006.01)
*C12P 1/00*   (2006.01)
*C12N 5/00*   (2006.01)
*C07K 14/005*   (2006.01)
*C12N 7/00*   (2006.01)

(52) U.S. Cl.
CPC ..... *C07K 14/005* (2013.01); *C12N 2710/14143* (2013.01); *C12N 2770/36151* (2013.01); *C12N 7/00* (2013.01); *C12N 2770/36163* (2013.01); *C12N 2770/36122* (2013.01); *A61K 39/12* (2013.01)
USPC .................. 424/218.1; 424/186.1; 424/192.1; 424/204.1; 435/41; 435/325

(58) Field of Classification Search
None
See application file for complete search history.

(56) References Cited

PUBLICATIONS

Saxena et al., Resurgence of chikungunya virus in India: an emerging threat, 2006, Eurosurveillance, vol. 11, No. 32, pp. 1-3.*
Weaver et al., Chikungunya virus and prospects for a vaccine, 2012, Expert Review Vaccines, vol. 11, No. 9, pp. 1087-1101.*
"Bac-to-Bac TOPO Expression System; An efficient site-specific transposition system to generate baculovirus for high-level expression of recombinant proteins," Version D, Invitrogen Corporation, Carlsbad, USA, Apr. 6, 2004. (updated version of manual enclosed).
Banerjee, K. and Ranadive, S.N., "Oligonucleotide fingerprinting of Chikungunya virus strains," Indian Jour. Med. Res., vol. 87, pp. 531-541, Jun. 1988.
Bedekar, S.D. and Pavri K.M., "Studies with Chikungunya Virus, Part I: Susceptibility of Birds and Small Mammals," Indian Jour. Med. Res., vol. 57, pp. 1181-1192, Jul. 1969.
Bedekar S.D. and Pavri K.M., "Studies with Chikungunya Virus, Part II: Serological Survey of Human and Animals in India," Indian Jour. Med. Res., vol. 57, pp. 1181-1992, Jul. 1969.
Chain, M.M.T., et al., "Morphological Development of Chikungunya Virus," Canadian Journal of Microbiology, vol. 12, pp. 895-899, 1966.
Chakravarthy, S.K., and Sarkar, J.K., "Susceptibility of New Born and Adult Laboratory Animals to Chikungunya Virus," Indian Jour. Med. Res., vol. 57, pp. 1157-1164, Jul. 1969.
Chaturvedi, U.C., et al., "Chikungunya Virus HI Antibodies in the Population of Lucknow and Kanpur," Indian Jour. Med. Res., vol. 58, pp. 297-301, Mar. 1970.
Eckels, K.H., et al., "Chikungunya Virus Vaccine Prepared by Tween-Ether Extraction," Applied Microbiology, vol. 19, No. 2, pp. 321-325, 1970.
Edelman, R. et al., "Phase II Safety and Immunogenicity Study of Live Chikungunya Virus Vaccine TSI-GSD-218," Am. Jour. Trop. Med. Hyg., vol. 62, pp. 681-685, 2000.
Giovarelli, M., et al., "Effect of Anti-μ- Chain-Specific Immunosuppression on Chikungunya Virus Encephalitis of Mice," Infection and Immunity, vol. 16, No. 3, pp. 849-852, Jun. 1977.
Hahon, N. and Hankins, W.A., "Assay of Chikungunya Virus in Cell Monolayers by Immunofluorescence," Applied Microbiology, vol. 19, No. 2, pp. 224-231, Feb. 1970.
Hahon, N. and Zimmerman, W.D., "Chikungunya Virus Infection of Cell Monoloyers by Cell-to Cell and Extracellular Transmission," Applied Microbiology, vol. 19, No. 2, pp. 389-391, Feb. 1970.
Claude Hannoun, "Arbovirus Haemagglutinins: Differential Susceptibility to Trypsin," Nature, vol. 219, pp. 753-755, Aug. 1968.

(Continued)

*Primary Examiner* — Benjamin P Blumel
(74) *Attorney, Agent, or Firm* — Roger D. Emerson; Peter R. Detorre; Emerson Thomson Bennett, LLC

(57) ABSTRACT

The present invention relates to vaccine formulation capable of eliciting protective immune response against Chikungunya virus infection in humans and other mammalian hosts. The immunogenic formulation comprises purified inactivated Chikungunya virus in a stable formulation. Methods of propagation and purification of the virus are discussed. The inactivated virus formulation is non-infectious, immunogenic and elicits protective immune response in mammalian host. The immunogenic composition is formulated for in vivo administration to humans. The invention also discusses the strategy of developing a subunit vaccine using the recombinant viral proteins as antigens for immunization. The recombinant virus antigens that are potentially immunogenic can be used in diagnosing for the presence of the virus.

14 Claims, 5 Drawing Sheets

(56) References Cited

PUBLICATIONS

Harrison, V.R., et al., "Comparative Immunogenicities of Chikungunya Vaccines Prepared in Avian and Mammalian Tissues," American Jour. Trop. Med. Hyg., vol. 16, No. 6. pp. 786-791, 1967.

Harrison, V.R., et al., "Production and Evaluation of a Formalin-Killed Chikungunya Vaccine," Journal of Immunology, vol. 107, No. 3, pp. 643-647, Sep. 1971.

Hearn, H.J. and Rainey, C.T., "Cross-Protection in Animals Infected with Group A Arboviruses," Journal of Immunology, vol. 90, pp. 720-724, 1963.

Heise, M.T., et al., "Sindbis-Group Alphavirus Replication in Periosteum and Endosteum of Long Bones in Adult Mice," Journal of Virology, vol. 74, No. 19, pp. 9294-9299, Oct. 2000.

Higashi, N., et al., "Electron Microscope Study of Development of Chikungunya Virus in Green Monkey Kidney Stable (VERO) Cells," Virology, vol. 33, pp. 55-69, 1967.

Khan, A.H., et al., "Complete nucleotide sequence of chikungunya virus and evidence for an internal polyadenylation site," Jour. Gen. Virol., vol. 83, pp. 3075-3084, 2002.

Klein, F., et al., "Concentration of Rift Valley Fever and Chikungunya Viruses by Precipitation," Applied Microbiology, vol. vol. 20, No. 3, pp. 346-350, Sep. 1970.

Lanciotti, R.S., et al., "Emergence of Epidemic O'nyong-nyong Fever in Uganda after a 35-Year Absence: Genetic Characterization of the Virus," Virology, vol. 252, pp. 258-268, 1998.

Levitt, N.H., et al., "Development of an attenuated strain of chikungunya virus for use in vaccine production," Vaccine, vol. 4, pp. 157-162, Sep. 1986.

McClain, D.J., et al., "Immunologic Interference from Sequential Administration of Live Attenuated Alphavirus Vaccines," Jour. Infect. Dis., vol. 177, pp. 634-641, 1998.

McIntosh, B.M., et al., "Further Studies on the Chikungunya Outbreak in Southern Rhodesia in 1962, I.—Mosquitoes, Wild Primates and Birds in Relation to the Epidemic," Ann. Trop. Med. Parasitol., vol. 58, pp. 45-51, rec'd for pub. Dec. 2, 1963.

Myers, R.M., "The 1964 Epidemic of Dengue-Like Fever in South India: Isolation of Chikungunya Virus from Human Sera and from Mosquitoes," Indian Jour. Med. Res., vol. 53, pp. 694-701, Aug. 1965.

Nimmannitya S., "Dengue and Chikungunya Virus Infection in Man in Thailand, 1962-1964," Am. Jour. Trop. Med. Hyg., vol. 18, No. 6, pp. 954-971, 1969.

Paul, S.D., and Singh, K.R.P., "Experimental Infection of *Macaca radiata* with Chikungunya Virus and Transmission of Virus by Mosquitoes," Indian Jour. Med. Res., vol. 56, pp. 802-810, Jun., 1968.

"Pichia Expression Kit; A Manual of Methods for Expression of Recombinant Proteins in *Pichia pastoris*," Version M, Catalog No. K1710-01, Invitrogen Corporation, Carlsbad, USA, Jan. 2002.

Porterfield, J.S., "Cross-Neutralization Studies with Group A Arthropod-borne Viruses," Bull WHO, vol. 24, pp. 735-741, 1961.

Powers. A.M., et al., "Re-emergence of chikungunya and o'nyong-nyong viruses: evidence for distinct geographical lineages and distant evolutionary relationships," Jour. Gen. Virol., vol. 81, pp. 471-479, 2000.

Price, W.H., "Studies on the Immunological Overlap Among Certain Arthropod-Borne Viruses, II.—The Role of Serologic Relationships in Experimental Vaccination Procedures," Am. Jour. Trop. Med. Hyg., vol. 67, pp. 115-121, 1958.

Ranadive, S.N. and Banarjee, K., "Cloning & expression of Chikungunya virus genes coding structural proteins in *Escherichia coli*," Indian Jour. Med. Res., vol. 91, pp. 386-392, Sep. 1990.
Rao, T.R., et al., "Preliminary Isolation and Identification of Chikungunya Virus from Cases of Dengue-Like Illness in Madras City," Indian Jour. Med. Res., vol. 53, pp. 689-693, Aug. 1965.
Ravi V., "Re-emergence of Chikungunya virus in India," Indian. Jour. Med. Microbiol., vol. 24, No. 2, pp. 83-84, 2006.
Sarkar, J.K., et al., "Haemorrhagic Fever in Calcutta: Some Epidemiological Observations," Indian Jour. Med. Res., vol. 52, pp. 651-659, Jul. 1964.
Sarkar, J.K., et al., "Chikungunya Virus Infection with Haemorrhagic Manifestations," Indian Jour. Med. Res., vol. 53, pp. 921-925, Oct. 1965.
Schuffenecker, I., et al., "Genome Microevolution of Chikungunya Viruses Causing the Indian Ocean Outbreak," PLOS Medicine, vol. 3, No. 7, e263, pp. 1058-1069, Jul. 2006.
Shaw, K.V., et al., "Virological Investigation of the Epidemic of Haemorrhagic Fever in Calcutta: Isolation of Three Strains of Chikungunya Virus," Indian Jour. Med. Res. , vol. 52, pp. 676-682, Jul. 1964.
Simizu, B., et al., "Structural Proteins of Chikungunya Virus," Jour. Virol., vol. 51, No. 1, pp. 254-258, Jul. 1984.
Umrigar, M.D., and Kadam, S.S., "Comparative Sensitivity of Suckling Mice and Vero Cells for Primary Isolation of Chikungunya Virus," Indian Jour. Med. Res., vol. 62, pp. 1893-1895, Dec. 1974.
Weiss, H.J., et al., "Hemorrhagic Disease in Rodents Caused by Chikungunya Virus, I.—Studies of Hemostasis," Proc. Soc. Exp. Biol. Med., vol. 119, pp. 427-432, 1965.
WHO Technical Report Series, No. 878, pp. 19-52, 1998.

* cited by examiner

SEQUENCE LISTING

<160> NUMBER OF SEQ ID NOS: 27

<210> SEQ ID NO 1
<211> LENGTH: 3747
<212> TYPE: DNA
<213> ORGANISM: Chikungunya virus

<400> SEQUENCE: 1

```
atggagttca tcccaaccca aactttttac aataggaggt accagcctcg accctggact      60
ccgcgctcta ctatccaaat catcaggccc agaccgcgcc ctcagaggca agctgggcaa     120
cttgcccagc tgatctcagc agttaataaa ctgacaatgc gcgcggtacc ccaacagaag     180
ccacgcagga atcggaagaa taagaagcaa aagcaaaaac aacaggcgcc acaaaacaac     240
acaaatcaaa agaagcagcc acctaaaaag aaaccggctc aaaagaaaaa gaagccgggc     300
cgcagagaga ggatgtgcat gaaaatcgaa aatgattgta ttttcgaagt caagcacgaa     360
ggtaaggtaa caggttacgc gtgcctggtg ggggacaaag taatgaaacc agcacacgta     420
aagggaccca tcgataacgc ggacctggcc aaactggcct ttaagcggtc atctaagtat     480
gaccttgaat gcgcgcagat acccgtgcac atgaagtccg acgcttcgaa gttcacccat     540
gagaaaccgg aggggtacta caactggcac cacggagcag tacagtactc aggaggccgg     600
ttcaccatcc ctacaggtgc tggcaaacca ggggacagcg gcagacctat cttcgacaac     660
aagggacgcg tggtggccat agtcttagga ggagctaatg aaggagcccg tacagccctc     720
tcggtggtga cctggaataa agacattgtc actaaaatca cccccgaggg ggccgaagag     780
tggagtcttg ccatcccagt tatgtgcctg ttggcaaaca ccacgttccc ctgctcccag     840
cccccttgca cgccctgctg ctacgaaaag gaaccggagg aaacccctacg catgcttgag     900
gacaacgtca tgagacctgg gtactatcag ctgctacaag catccttaac atgttctccc     960
caccgccagc gacgcagcac caaggacaac ttcaatgtct ataaagccac aagaccatac    1020
ttagctcact gtcccgactg tggagaaggg cactcgtgcc atagtcccgt agcactagaa    1080
cgcatcagaa atgaagcgac agacgggacg ctgaaaatcc aggtctcctt gcaaatcgga    1140
ataaagacgg atgacagcca cgattggacc aagctgcgtt atatggacaa ccacatgcca    1200
gcagacgcag agagggcggg gctatttgta agaacatcag caccgtgtac gattactgga    1260
acaatgggac acttcatcct ggcccgatgt ccaaaagggg aaactctgac ggtgggattc    1320
actgacagta ggaagattag tcactcatgt acgcacccat tcaccacga ccctcctgtg    1380
ataggtcggg aaaaattcca ttcccgaccg cagcacggta aagagctacc ttgcagcacg    1440
tacgtgcaga gcaccgccgc aactaccgag agatagagg tacacatgcc cccagacacc    1500
cctgatcgca cattaatgtc acaacagtcc ggcaacgtaa agatcacagt caatggccag    1560
acggtgcggt acaagtgtaa ttgcggtggc tcaaatgaag gactaacaac tacagacaaa    1620
gtgattaata actgcaaggt tgatcaatgt catgccgcgg tcaccaatca caaaaagtgg    1680
cagtataact ccctctggt cccgcgtaat gctgaacttg gggaccgaaa aggaaaaatt    1740
cacatcccgt ttccgctggc aaatgtaaca tgcagggtgc ctaaagcaag gaaccccacc    1800
```

| | |
|---|---|
| gtgacgtacg ggaaaaacca agtcatcatg ctactgtatc ctgaccaccc aacactcctg | 1860 |
| tcctaccgga atatgggaga agaaccaaac tatcaagaag agtgggtgat gcataagaag | 1920 |
| gaagtcgtgc taaccgtgcc gactgaaggg ctcgaggtca cgtggggcaa caacgagccg | 1980 |
| tataagtatt ggccgcagtt atctacaaac ggtacagccc atggccaccc gcatgagata | 2040 |
| attctgtatt attatgagct gtaccccact atgactgtag tagttgtgtc agtggccacg | 2100 |
| ttcatactcc tgtcgatggt gggtatggca gcggggatgt gcatgtgtgc acgacgcaga | 2160 |
| tgcatcacac cgtatgaact gacaccagga gctaccgtcc ctttcctgct tagcctaata | 2220 |
| tgctgcatca gaacagctaa agcggccaca taccaagagg ctgcgatata cctgtggaac | 2280 |
| gagcagcaac ctttgttttg gctacaagcc cttattccgc tggcagccct gattgttcta | 2340 |
| tgcaactgtc tgagactctt accatgctgc tgtaaaacgt tggctttttt agccgtaatg | 2400 |
| agcgtcggtg cccacactgt gagcgcgtac gaacacgtaa cagtgatccc gaacacggtg | 2460 |
| ggagtaccgt ataagactct agtcaataga cctggctaca gccccatggt attggagatg | 2520 |
| gaactactgt cagtcacttt ggagccaaca ctatcgcttg attacatcac gtgcgagtac | 2580 |
| aaaaccgtca tcccgtctcc gtacgtgaag tgctgcggta cagcagagtg caaggacaaa | 2640 |
| aacctacctg actacagctg tagggtcttc accggcgtct acccatttat gtggggtggc | 2700 |
| gcctactgct tctgcgacgc tgaaaacacg cagttgagcg aagcacatgt ggagaagtcc | 2760 |
| gaatcatgca aaacagaatt tgcatcagca tacagggctc ataccgcatc tgcatcagct | 2820 |
| aagctccgcg tcctttacca aggaaataac atcactgtaa ctgcctatgc aaacggcgac | 2880 |
| catgccgtca cagttaagga cgccaaattc attgtgggc caatgtcttc agcctggaca | 2940 |
| cctttcgaca caaaattgt ggtgtacaaa ggtgacgtct ataacatgga ctacccgccc | 3000 |
| tttggcgcag aagaccagg acaatttggc gatatccaaa gtcgcacacc tgagagtaaa | 3060 |
| gacgtctatg ctaatacaca actggtactg cagagaccgg ctgcgggtac ggtacacgtg | 3120 |
| ccatactctc aggcaccatc tggctttaag tattggctaa agaacgcgg ggcgtcactg | 3180 |
| cagcacacag caccatttgg ctgccaaata gcaacaaacc cggtaagagc ggtgaactgc | 3240 |
| gccgtaggga acatgcccat ctccatcgac ataccggaag cggccttcac tagggtcgtc | 3300 |
| gacgcgccct ctttaacgga catgtcgtgc gaggtaccag cctgcaccca ttcctcagac | 3360 |
| tttgggggcg tcgccattat taaatatgca gccagcaaga aggcaagtg tgcggtgcat | 3420 |
| tcgatgacta acgccgtcac tattcgggaa gctgagatag aagttgaagg gaattctcag | 3480 |
| ctgcaaatct ctttctcgac ggccttagcc agcgccgaat ccgcgtaca agtctgttct | 3540 |
| acacaagtac actgtgcagc tgagtgccac cccccgaagg accacatagt caactacccg | 3600 |
| gcgtcacata ccaccctcgg ggtccaggac atctccgcta cggcgatgtc atgggtgcag | 3660 |
| aagatcacgg gaggtgtggg actggttgtt gctgttgccg cactgattct aatcgtggtg | 3720 |
| ctatgcgtgt cgttcagcag gcactaa | 3747 |

<210> SEQ ID NO 2
<211> LENGTH: 3750
<212> TYPE: DNA
<213> ORGANISM: Chikungunya virus

<400> SEQUENCE: 2

| | |
|---|---|
| accatggagt tcatcccaac ccaaactttt tacaatagga ggtaccagcc tcgaccctgg | 60 |
| actccgcgct ctactatcca aatcatcagg cccagaccgc gccctcagag gcaagctggg | 120 |
| caacttgccc agctgatctc agcagttaat aaaactgacaa tgcgcgcggt accccaacag | 180 |

```
aagccacgca ggaatcggaa gaataagaag caaaagcaaa acaacaggc gccacaaaac    240 aacacaaatc aaaagaagca gccacctaaa aagaaaccgg ctcaaaagaa aaagaagccg    300
ggccgcagag agaggatgtg catgaaaatc gaaaatgatt gtattttcga agtcaagcac    360
gaaggtaagg taacaggtta cgcgtgcctg gtggggaca aagtaatgaa accagcacac     420
gtaaagggga ccatcgataa cgcggacctg gccaaactgg cctttaagcg gtcatctaag    480
tatgaccttg aatgcgcgca gatacccgtg cacatgaagt ccgacgcttc gaagttcacc    540
catgagaaac cggaggggta ctacaactgg caccacggag cagtacagta ctcaggaggc    600
cggttcacca tccctacagg tgctggcaaa ccaggggaca gcggcagacc tatcttcgac    660
aacaagggac gcgtggtggc catagtctta ggaggagcta atgaaggagc ccgtacagcc    720
ctctcggtgg tgacctggaa taaagacatt gtcactaaaa tcaccccgga gggggccgaa    780
gagtggagtc ttgccatccc agttatgtgc ctgttggcaa acaccacgtt ccctgctcc     840 cagcccctt gcacgccctg ctgctacgaa aaggaaccgg aggaaaccct acgcatgctt    900
gaggacaacg tcatgagacc tgggtactat cagctgctac aagcatcctt aacatgttct    960
ccccaccgcc agcgacgcag caccaaggac aacttcaatg tctataaagc cacaagacca   1020
tacttagctc actgtcccga ctgtggagaa gggcactcgt gccatagtcc cgtagcacta   1080
gaacgcatca gaaatgaagc gacagacggg acgctgaaaa tccaggtctc cttgcaaatc   1140
ggaataaaga cggatgacag ccacgattgg accaagctgc gttatatgga caaccacatg   1200
ccagcagacg cagagagggc ggggctatttt gtaagaacat cagcaccgtg tacgattact   1260
ggaacaatgg gacacttcat cctggcccga tgtccaaaag gggaaactct gacggtggga   1320
ttcactgaca gtaggaagat tagtcactca tgtacgcacc catttcacca cgaccctcct   1380
gtgataggtc gggaaaaatt ccattcccga ccgcagcacg gtaaagagct accttgcagc   1440
acgtacgtgc agagcaccgc cgcaactacc gaggagatag aggtacacat gcccccagac   1500 accccctgatc gcacattaat gtcacaacag tccggcaacg taaagatcac agtcaatggc   1560
cagacggtgc ggtacaagtg taattgcggt ggctcaaatg aaggactaac aactacagac   1620
aaagtgatta ataactgcaa ggttgatcaa tgtcatgccg cggtcaccaa tcacaaaaag   1680
tggcagtata actcccctct ggtcccgcgt aatgctgaac ttgggaccg aaaaggaaaa    1740 attcacatcc cgtttccgct ggcaaatgta acatgcaggg tgcctaaagc aaggaacccc   1800
accgtgacgt acgggaaaaa ccaagtcatc atgctactgt atcctgacca cccaacactc   1860
ctgtcctacc ggaatatggg agaagaacca aactatcaag aagagtgggt gatgcataag   1920
aaggaagtcg tgctaaccgt gccgactgaa gggctcgagg tcacgtgggg caacaacgag   1980
ccgtataagt attggcgcca gttatctaca acggtacag cccatggcca cccgcatgag    2040
ataattctgt attattatga gctgtacccc actatgactg tagtagttgt gtcagtggcc    2100
acgttcatac tcctgtcgat ggtgggtatg gcagcgggga tgtgcatgtg tgcacgacgc    2160
agatgcatca caccgtatga actgacacca ggagctaccg tccctttcct gcttagccta    2220
atatgctgca tcagaacagc taaagcggcc acataccaag aggctgcgat atacctgtgg    2280
aacgagcagc aaccttttgt tggctacaa gcccttattc cgctggcagc cctgattgtt    2340
ctatgcaact gtctgagact cttaccatgc tgctgtaaaa cgttggcttt tttagccgta   2400
atgagcgtcg tgcccacac tgtgagcgcg tacgaacacg taacagtgat cccgaacacg    2460
gtgggagtac cgtataagac tctagtcaat agacctggct acagcccat ggtattggag    2520
```

| | |
|---|---|
| atggaactac tgtcagtcac tttggagcca acactatcgc ttgattacat cacgtgcgag | 2580 |
| tacaaaaccg tcatcccgtc tccgtacgtg aagtgctgcg gtacagcaga gtgcaaggac | 2640 |
| aaaaacctac ctgactacag ctgtagggtc ttcaccggcg tctacccatt tatgtgggt | 2700 |
| ggcgcctact gcttctgcga cgctgaaaac acgcagttga gcgaagcaca tgtggagaag | 2760 |
| tccgaatcat gcaaaacaga atttgcatca gcatacaggg ctcataccgc atctgcatca | 2820 |
| gctaagctcc gcgtccttta ccaaggaaat aacatcactg taactgccta tgcaaacggc | 2880 |
| gaccatgccg tcacagttaa ggacgccaaa ttcattgtgg ggccaatgtc ttcagcctgg | 2940 |
| acacctttcg acaacaaaat tgtggtgtac aaaggtgacg tctataacat ggactacccg | 3000 |
| ccctttggcg caggaagacc aggacaattt ggcgatatcc aaagtcgcac acctgagagt | 3060 |
| aaagacgtct atgctaatac acaactggta ctgcagagac cggctgcggg tacggtacac | 3120 |
| gtgccatact ctcaggcacc atctggcttt aagtattggc taaaagaacg cggggcgtca | 3180 |
| ctgcagcaca cagcaccatt tggctgccaa atagcaacaa accccggtaag agcggtgaac | 3240 |
| tgcgccgtag ggaacatgcc catctccatc gacataccgg aagcggcctt cactagggtc | 3300 |
| gtcgacgcgc cctctttaac ggacatgtcg tgcgaggtac cagcctgcac ccattcctca | 3360 |
| gactttgggg gcgtcgccat tattaaatat gcagccagca gaaaaggcaa gtgtgcggtg | 3420 |
| cattcgatga ctaacgccgt cactattcgg gaagctgaga tagaagttga agggaattct | 3480 |
| cagctgcaaa tctcttttct gacggcctta gccagcgccg aattccgcgt acaagtctgt | 3540 |
| tctacacaag tacactgtgc agctgagtgc caccccccga aggaccacat agtcaactac | 3600 |
| ccggcgtcac ataccaccct cggggtccag gacatctccg ctacggcgat gtcatgggtg | 3660 |
| cagaagatca cgggaggtgt gggactggtt gttgctgttg ccgcactgat tctaatcgtg | 3720 |
| gtgctatgcg tgtcgttcag caggcactaa | 3750 |

<210> SEQ ID NO 3
<211> LENGTH: 3697
<212> TYPE: DNA
<213> ORGANISM: Chikungunya virus

<400> SEQUENCE: 3

| | |
|---|---|
| tactatccaa atcatcaggc ccagaccgcg ccctcagagg caagctgggc aacttgccca | 60 |
| gctgatctca gcagttaata aactgacaat gcgcgcggta ccccaacaga agccacgcag | 120 |
| gaatcggaag aataagaagc aaaagcaaaa acaacaggcg ccacaaaaca cacaaatca | 180 |
| aaagaagcag ccacctaaaa agaaaccggc tcaaaagaaa aagaagccgg ccgcagagaa | 240 |
| gaggatgtgc atgaaaatcg aaaatgattg tattttcgaa gtcaagcacg aaggtaaggt | 300 |
| aacaggttac gcgtgcctgg tggggacaa agtaatgaaa ccagcacacg taaaggggac | 360 |
| catcgataac gcggacctgg ccaaactggc ctttaagcgg tcatctaagt atgaccttga | 420 |
| atgcgcgcag ataccgtgc acatgaagtc cgacgcttcg aagttcaccc atgagaaacc | 480 |
| ggagggtac tacaactggc accacggagc agtacagtac tcaggaggcc ggttcaccat | 540 |
| ccctacaggt gctggcaaac aggggacag cggcagacct atcttcgaca acaagggacg | 600 |
| cgtggtggcc atagtcttag gaggagctaa tgaaggagcc cgtacagccc tctcggtggt | 660 |
| gacctggaat aaagacattg tcactaaaat caccccgag ggggccgaag agtggagtct | 720 |
| tgccatccca gttatgtgcc tgttggcaaa caccacgttc ccctgctccc agccccttg | 780 |
| cacgccctgc tgctacgaaa aggaaccgga ggaaaccta cgcatgcttg aggacaacgt | 840 |
| catgagacct gggtactatc agctgctaca agcatcctta acatgttctc cccaccgcca | 900 |

```
gcgacgcagc accaaggaca acttcaatgt ctataaagcc acaagaccat acttagctca      960
ctgtcccgac tgtggagaag ggcactcgtg ccatagtccc gtagcactag aacgcatcag     1020
aaatgaagcg acagacggga cgctgaaaat ccaggtctcc ttgcaaatcg aataaagac      1080 ggatgacagc cacgattgga ccaagctgcg ttatatggac aaccacatgc cagcagacgc     1140
agagagggcg gggctatttg taagaacatc agcaccgtgt acgattactg aacaatggg      1200 acacttcatc ctggcccgat gtccaaaagg ggaaactctg acggtgggat tcactgacag     1260
taggaagatt agtcactcat gtacgcaccc atttcaccac gaccctcctg tgataggtcg     1320
ggaaaaattc cattcccgac cgcagcacgg taaagagcta ccttgcagca cgtacgtgca     1380
gagcaccgcc gcaactaccg aggagataga ggtacacatg ccccagaca ccctgatcg      1440 cacattaatg tcacaacagt ccggcaacgt aaagatcaca gtcaatggcc agacggtgcg     1500
gtacaagtgt aattgcggtg gctcaaatga aggactaaca actacagaca aagtgattaa     1560
taactgcaag gttgatcaat gtcatgccgc ggtcaccaat cacaaaaagt ggcagtataa     1620
ctcccctctg gtcccgcgta atgctgaact tggggaccga aaaggaaaaa ttcacatccc     1680
gtttccgctg gcaaatgtaa catgcagggt gcctaaagca aggaacccca ccgtgacgta     1740
cgggaaaaac caagtcatca tgctactgta tcctgaccac ccaacactcc tgtcctaccg     1800
gaatatggga gaagaaccaa actatcaaga gagtgggtg atgcataaga aggaagtcgt      1860
gctaaccgtg ccgactgaag ggctcgaggt cacgtggggc aacaacgagc cgtataagta     1920
ttggccgcag ttatctacaa acggtacagc ccatggccac ccgcatgaga taattctgta     1980
ttattatgag ctgtaccca ctatgactgt agtagttgtg tcagtggcca cgttcatact      2040
cctgtcgatg gtgggtatgg cagcggggat gtgcatgtgt gcacgacgca gatgcatcac     2100
accgtatgaa ctgacaccag gagctaccgt ccctttcctg cttagcctaa tatgctgcat     2160
cagaacagct aaagcggcca cataccaaga ggctgcgata tacctgtgga acgagcagca     2220
acctttgttt tggctacaag cccttattcc gctggcagcc ctgattgttc tatgcaactg     2280
tctgagactc ttaccatgct gctgtaaaac gttggctttt ttagccgtaa tgagcgtcgg     2340
tgcccacact gtgagcgcgt acgaacacgt aacagtgatc ccgaacacgg tgggagtacc     2400
gtataagact ctagtcaata gacctggcta cagccccatg gtattggaga tggaactact     2460
gtcagtcact ttggagccaa cactatcgct tgattacatc acgtgcgagt acaaaaccgt     2520
catcccgtct ccgtacgtga agtgctgcgg tacagcagag tgcaaggaca aaaacctacc     2580
tgactacagc tgtagggtct tcaccggcgt ctacccattt atgtggggtg cgcctactg     2640 cttctgcgac gctgaaaaca cgcagttgag cgaagcacat gtggagaagt ccgaatcatg     2700
caaaacagaa tttgcatcag catacagggc tcataccgca tctgcatcag ctaagctccg     2760
cgtcctttac caaggaaata acatcactgt aactgcctat gcaaacggcg accatgccgt     2820
cacagttaag gacgccaaat tcattgtggg gccaatgtct tcagcctgga caccttttcga    2880 caacaaatt gtggtgtaca aggtgacgt ctataacatg gactacccgc cctttggcgc       2940
aggaagacca ggacaattg gcgatatcca aagtcgcaca cctgagagta aagacgtcta      3000 tgctaatacan caactggtac tgcagagacc ggctgcgggt acgtacacg tgccatactc     3060 tcaggcacca tctggctta agtattggct aaaagaacgc ggggcgtcac tgcagcacac     3120
agcaccattt ggctgccaaa tagcaacaaa cccggtaaga gcggtgaact gcgccgtagg     3180
gaacatgccc atctccatcg acataccgga agcggccttc actagggtcg tcgacgcgcc     3240
```

-continued

```
ctctttaacg acatgtcgt gcgaggtacc agcctgcacc cattcctcag actttggggg    3300
cgtcgccatt attaaatatg cagccagcaa gaaaggcaag tgtgcggtgc attcgatgac    3360
taacgccgtc actattcggg aagctgagat agaagttgaa gggaattctc agctgcaaat    3420
ctctttctcg acggcttag ccagcgccga attccgcgta caagtctgtt ctacacaagt     3480
acactgtgca gctgagtgcc accccccgaa ggaccacata gtcaactacc cggcgtcaca    3540
taccaccctc gggtccagg acatctccgc tacggcgatg tcatgggtgc agaagatcac     3600
gggaggtgtg ggactggttg ttgctgttgc cgcactgatt ctaatcgtgg tgctatgcgt    3660
gtcgttcagc aggcaccatc accatcacca tcactaa                             3697
```

<210> SEQ ID NO 4
<211> LENGTH: 1248
<212> TYPE: PRT
<213> ORGANISM: Chikungunya virus

<400> SEQUENCE: 4

```
Met Glu Phe Ile Pro Thr Gln Thr Phe Tyr Asn Arg Arg Tyr Gln Pro
1               5                   10                  15

Arg Pro Trp Thr Pro Arg Ser Thr Ile Gln Ile Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
50                  55                  60

Arg Lys Asn Lys Lys Gln Lys Gln Lys Gln Ala Pro Gln Asn Asn
65                  70                  75                  80

Thr Asn Gln Lys Lys Gln Pro Pro Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Ile Pro Val Met Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Glu Thr Leu Arg Met Leu Glu Asp Asn Val Met
```

```
            290                 295                 300
Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
                340                 345                 350

Cys His Ser Pro Val Ala Leu Glu Arg Ile Arg Asn Glu Ala Thr Asp
                355                 360                 365

Gly Thr Leu Lys Ile Gln Val Ser Leu Gln Ile Gly Ile Lys Thr Asp
            370                 375                 380

Asp Ser His Asp Trp Thr Lys Leu Arg Tyr Met Asp Asn His Met Pro
385                 390                 395                 400

Ala Asp Ala Glu Arg Ala Gly Leu Phe Val Arg Thr Ser Ala Pro Cys
                405                 410                 415

Thr Ile Thr Gly Thr Met Gly His Phe Ile Leu Ala Arg Cys Pro Lys
                420                 425                 430

Gly Glu Thr Leu Thr Val Gly Phe Thr Asp Ser Arg Lys Ile Ser His
                435                 440                 445

Ser Cys Thr His Pro Phe His His Asp Pro Val Ile Gly Arg Glu
            450                 455                 460

Lys Phe His Ser Arg Pro Gln His Gly Lys Glu Leu Pro Cys Ser Thr
465                 470                 475                 480

Tyr Val Gln Ser Thr Ala Ala Thr Thr Glu Glu Ile Glu Val His Met
                485                 490                 495

Pro Pro Asp Thr Pro Asp Arg Thr Leu Met Ser Gln Gln Ser Gly Asn
                500                 505                 510

Val Lys Ile Thr Val Asn Gly Gln Thr Val Arg Tyr Lys Cys Asn Cys
            515                 520                 525

Gly Gly Ser Asn Glu Gly Leu Thr Thr Thr Asp Lys Val Ile Asn Asn
            530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
                580                 585                 590

Val Pro Lys Ala Arg Asn Pro Thr Val Thr Tyr Gly Lys Asn Gln Val
                595                 600                 605

Ile Met Leu Leu Tyr Pro Asp His Pro Thr Leu Leu Ser Tyr Arg Asn
            610                 615                 620

Met Gly Glu Glu Pro Asn Tyr Gln Glu Glu Trp Val Met His Lys Lys
625                 630                 635                 640

Glu Val Val Leu Thr Val Pro Thr Glu Gly Leu Glu Val Thr Trp Gly
                645                 650                 655

Asn Asn Glu Pro Tyr Lys Tyr Trp Pro Gln Leu Ser Thr Asn Gly Thr
                660                 665                 670

Ala His Gly His Pro His Glu Ile Ile Leu Tyr Tyr Tyr Glu Leu Tyr
                675                 680                 685

Pro Thr Met Thr Val Val Val Ser Val Ala Thr Phe Ile Leu Leu
            690                 695                 700

Ser Met Val Gly Met Ala Ala Gly Met Cys Met Cys Ala Arg Arg Arg
705                 710                 715                 720
```

```
Cys Ile Thr Pro Tyr Glu Leu Thr Pro Gly Ala Thr Val Pro Phe Leu
            725                 730                 735

Leu Ser Leu Ile Cys Cys Ile Arg Thr Ala Lys Ala Ala Thr Tyr Gln
            740                 745                 750

Glu Ala Ala Ile Tyr Leu Trp Asn Glu Gln Gln Pro Leu Phe Trp Leu
            755                 760                 765

Gln Ala Leu Ile Pro Leu Ala Ala Leu Ile Val Leu Cys Asn Cys Leu
            770                 775                 780

Arg Leu Leu Pro Cys Cys Cys Lys Thr Leu Ala Phe Leu Ala Val Met
785                 790                 795                 800

Ser Val Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
                820                 825                 830

Tyr Ser Pro Met Val Leu Glu Met Glu Leu Leu Ser Val Thr Leu Glu
                835                 840                 845

Pro Thr Leu Ser Leu Asp Tyr Ile Thr Cys Glu Tyr Lys Thr Val Ile
        850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Arg Val Phe Thr Gly Val Tyr Pro Phe
                885                 890                 895

Met Trp Gly Gly Ala Tyr Cys Phe Cys Asp Ala Glu Asn Thr Gln Leu
                900                 905                 910

Ser Glu Ala His Val Glu Lys Ser Glu Ser Cys Lys Thr Glu Phe Ala
                915                 920                 925

Ser Ala Tyr Arg Ala His Thr Ala Ser Ala Ser Ala Lys Leu Arg Val
        930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                965                 970                 975

Ser Ala Trp Thr Pro Phe Asp Asn Lys Ile Val Val Tyr Lys Gly Asp
                980                 985                 990

Val Tyr Asn Met Asp Tyr Pro Pro Phe Gly Ala Gly Arg Pro Gly Gln
        995                 1000                1005

Phe Gly Asp Ile Gln Ser Arg Thr Pro Glu Ser Lys Asp Val Tyr
        1010                1015                1020

Ala Asn Thr Gln Leu Val Leu Gln Arg Pro Ala Ala Gly Thr Val
        1025                1030                1035

His Val Pro Tyr Ser Gln Ala Pro Ser Gly Phe Lys Tyr Trp Leu
        1040                1045                1050

Lys Glu Arg Gly Ala Ser Leu Gln His Thr Ala Pro Phe Gly Cys
        1055                1060                1065

Gln Ile Ala Thr Asn Pro Val Arg Ala Val Asn Cys Ala Val Gly
        1070                1075                1080

Asn Met Pro Ile Ser Ile Asp Ile Pro Glu Ala Ala Phe Thr Arg
        1085                1090                1095

Val Val Asp Ala Pro Ser Leu Thr Asp Met Ser Cys Glu Val Pro
        1100                1105                1110

Ala Cys Thr His Ser Ser Asp Phe Gly Gly Val Ala Ile Ile Lys
        1115                1120                1125
```

-continued

```
Tyr Ala Ala Ser Lys Lys Gly Lys Cys Ala Val His Ser Met Thr
        1130                1135                1140

Asn Ala Val Thr Ile Arg Glu Ala Glu Ile Glu Val Glu Gly Asn
    1145                1150                1155

Ser Gln Leu Gln Ile Ser Phe Ser Thr Ala Leu Ala Ser Ala Glu
    1160                1165                1170

Phe Arg Val Gln Val Cys Ser Thr Gln Val His Cys Ala Ala Glu
    1175                1180                1185

Cys His Pro Pro Lys Asp His Ile Val Asn Tyr Pro Ala Ser His
    1190                1195                1200

Thr Thr Leu Gly Val Gln Asp Ile Ser Ala Thr Ala Met Ser Trp
    1205                1210                1215

Val Gln Lys Ile Thr Gly Gly Val Gly Leu Val Val Ala Val Ala
    1220                1225                1230

Ala Leu Ile Leu Ile Val Val Leu Cys Val Ser Phe Ser Arg His
    1235                1240                1245

<210> SEQ ID NO 5
<211> LENGTH: 1254
<212> TYPE: PRT
<213> ORGANISM: Chikungunya virus

<400> SEQUENCE: 5

Met Glu Phe Ile Pro Thr Gln Thr Phe Tyr Asn Arg Arg Tyr Gln Pro
1               5                   10                  15

Arg Pro Trp Thr Pro Arg Ser Thr Ile Gln Ile Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Lys Gln Lys Gln Ala Pro Gln Asn Asn
65                  70                  75                  80

Thr Asn Gln Lys Lys Gln Pro Pro Lys Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255
```

```
Gly Ala Glu Glu Trp Ser Leu Ala Ile Pro Val Met Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Thr Leu Arg Met Leu Glu Asp Asn Val Met
290                 295                 300

Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
        340                 345                 350

Cys His Ser Pro Val Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Asn His Met Pro
385                 390                 395                 400

Ala Asp Ala Glu Arg Ala Gly Leu Phe Val Arg Thr Ser Ala Pro Cys
                405                 410                 415

Thr Ile Thr Gly Thr Met Gly His Phe Ile Leu Ala Arg Cys Pro Lys
        420                 425                 430

Gly Glu Thr Leu Thr Val Gly Phe Thr Asp Ser Arg Lys Ile Ser His
        435                 440                 445

Ser Cys Thr His Pro Phe His His Asp Pro Pro Val Ile Gly Arg Glu
    450                 455                 460

Lys Phe His Ser Arg Pro Gln His Gly Lys Glu Leu Pro Cys Ser Thr
465                 470                 475                 480

Tyr Val Gln Ser Thr Ala Ala Thr Thr Glu Glu Ile Glu Val His Met
            485                 490                 495

Pro Pro Asp Thr Pro Asp Arg Thr Leu Met Ser Gln Gln Ser Gly Asn
                500                 505                 510

Val Lys Ile Thr Val Asn Gly Gln Thr Val Arg Tyr Lys Cys Asn Cys
        515                 520                 525

Gly Gly Ser Asn Glu Gly Leu Thr Thr Thr Asp Lys Val Ile Asn Asn
    530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
            565                 570                 575

Lys Gly Lys Ile His Ile Pro Phe Pro Leu Ala Asn Val Thr Cys Arg
            580                 585                 590

Val Pro Lys Ala Arg Asn Pro Thr Val Thr Tyr Gly Lys Asn Gln Val
        595                 600                 605

Ile Met Leu Leu Tyr Pro Asp His Pro Thr Leu Leu Ser Tyr Arg Asn
        610                 615                 620

Met Gly Glu Glu Pro Asn Tyr Gln Glu Glu Trp Val Met His Lys Lys
625                 630                 635                 640

Glu Val Val Leu Thr Val Pro Thr Glu Gly Leu Glu Val Thr Trp Gly
                645                 650                 655

Asn Asn Glu Pro Tyr Lys Tyr Trp Pro Gln Leu Ser Thr Asn Gly Thr
            660                 665                 670
```

```
Ala His Gly His Pro His Glu Ile Ile Leu Tyr Tyr Glu Leu Tyr
        675                 680                 685
Pro Thr Met Thr Val Val Val Ser Val Ala Thr Phe Ile Leu Leu
    690                 695                 700
Ser Met Val Gly Met Ala Ala Gly Met Cys Met Cys Ala Arg Arg Arg
705                 710                 715                 720
Cys Ile Thr Pro Tyr Glu Leu Thr Pro Gly Ala Thr Val Pro Phe Leu
                725                 730                 735
Leu Ser Leu Ile Cys Cys Ile Arg Thr Ala Lys Ala Ala Thr Tyr Gln
            740                 745                 750
Glu Ala Ala Ile Tyr Leu Trp Asn Glu Gln Pro Leu Phe Trp Leu
        755                 760                 765
Gln Ala Leu Ile Pro Leu Ala Ala Leu Ile Val Leu Cys Asn Cys Leu
    770                 775                 780
Arg Leu Leu Pro Cys Cys Cys Lys Thr Leu Ala Phe Leu Ala Val Met
785                 790                 795                 800
Ser Val Gly Ala His Thr Val Ser Ala Tyr Glu His Val Thr Val Ile
                805                 810                 815
Pro Asn Thr Val Gly Val Pro Tyr Lys Thr Leu Val Asn Arg Pro Gly
            820                 825                 830
Tyr Ser Pro Met Val Leu Glu Met Glu Leu Leu Ser Val Thr Leu Glu
        835                 840                 845
Pro Thr Leu Ser Leu Asp Tyr Ile Thr Cys Glu Tyr Lys Thr Val Ile
    850                 855                 860
Pro Ser Pro Tyr Val Lys Cys Cys Gly Thr Ala Glu Cys Lys Asp Lys
865                 870                 875                 880
Asn Leu Pro Asp Tyr Ser Cys Arg Val Phe Thr Gly Val Tyr Pro Phe
                885                 890                 895
Met Trp Gly Gly Ala Tyr Cys Phe Cys Asp Ala Glu Asn Thr Gln Leu
            900                 905                 910
Ser Glu Ala His Val Glu Lys Ser Glu Ser Cys Lys Thr Glu Phe Ala
        915                 920                 925
Ser Ala Tyr Arg Ala His Thr Ala Ser Ala Ser Ala Lys Leu Arg Val
    930                 935                 940
Leu Tyr Gln Gly Asn Asn Ile Thr Val Thr Ala Tyr Ala Asn Gly Asp
945                 950                 955                 960
His Ala Val Thr Val Lys Asp Ala Lys Phe Ile Val Gly Pro Met Ser
                965                 970                 975
Ser Ala Trp Thr Pro Phe Asp Asn Lys Ile Val Val Tyr Lys Gly Asp
            980                 985                 990
Val Tyr Asn Met Asp Tyr Pro Pro Phe Gly Ala Gly Arg Pro Gly Gln
        995                 1000                1005
Phe Gly Asp Ile Gln Ser Arg Thr Pro Glu Ser Lys Asp Val Tyr
    1010                1015                1020
Ala Asn Thr Gln Leu Val Leu Gln Arg Pro Ala Ala Gly Thr Val
    1025                1030                1035
His Val Pro Tyr Ser Gln Ala Pro Ser Gly Phe Lys Tyr Trp Leu
    1040                1045                1050
Lys Glu Arg Gly Ala Ser Leu Gln His Thr Ala Pro Phe Gly Cys
    1055                1060                1065
Gln Ile Ala Thr Asn Pro Val Arg Ala Val Asn Cys Ala Val Gly
    1070                1075                1080
Asn Met Pro Ile Ser Ile Asp Ile Pro Glu Ala Ala Phe Thr Arg
```

```
                    1085                1090                1095
Val Val Asp Ala Pro Ser Leu Thr Asp Met Ser Cys Glu Val Pro
        1100                1105                1110

Ala Cys Thr His Ser Ser Asp Phe Gly Gly Val Ala Ile Ile Lys
        1115                1120                1125

Tyr Ala Ala Ser Lys Lys Gly Lys Cys Ala Val His Ser Met Thr
        1130                1135                1140

Asn Ala Val Thr Ile Arg Glu Ala Glu Ile Glu Val Glu Gly Asn
        1145                1150                1155

Ser Gln Leu Gln Ile Ser Phe Ser Thr Ala Leu Ala Ser Ala Glu
        1160                1165                1170

Phe Arg Val Gln Val Cys Ser Thr Gln Val His Cys Ala Ala Glu
        1175                1180                1185

Cys His Pro Pro Lys Asp His Ile Val Asn Tyr Pro Ala Ser His
        1190                1195                1200

Thr Thr Leu Gly Val Gln Asp Ile Ser Ala Thr Ala Met Ser Trp
        1205                1210                1215

Val Gln Lys Ile Thr Gly Gly Val Gly Leu Val Val Ala Val Ala
        1220                1225                1230

Ala Leu Ile Leu Ile Val Val Leu Cys Val Ser Phe Ser Arg His
        1235                1240                1245

His His His His His
        1250

<210> SEQ ID NO 6
<211> LENGTH: 267
<212> TYPE: PRT
<213> ORGANISM: Chikungunya virus

<400> SEQUENCE: 6

Met Glu Phe Ile Pro Thr Gln Thr Phe Tyr Asn Arg Arg Tyr Gln Pro
1               5                   10                  15

Arg Pro Trp Thr Pro Arg Ser Thr Ile Gln Ile Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Lys Gln Lys Gln Ala Pro Gln Asn Asn
65                  70                  75                  80

Thr Asn Gln Lys Lys Gln Pro Pro Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Thr Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190
```

```
Ala Val Gln Tyr Ser Gly Gly Arg Phe Thr Ile Pro Thr Gly Ala Gly
            195                 200                 205

Lys Pro Gly Asp Ser Gly Arg Pro Ile Phe Asp Asn Lys Gly Arg Val
210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp His His His His His His
            260                 265

<210> SEQ ID NO 7
<211> LENGTH: 71
<212> TYPE: PRT
<213> ORGANISM: Chikungunya virus

<400> SEQUENCE: 7

Met Ser Leu Ala Ile Pro Val Met Cys Leu Leu Ala Asn Thr Thr Phe
1               5                   10                  15

Pro Cys Ser Gln Pro Pro Cys Thr Pro Cys Cys Tyr Glu Lys Glu Pro
            20                  25                  30

Glu Glu Thr Leu Arg Met Leu Glu Asp Asn Val Met Arg Pro Gly Tyr
        35                  40                  45

Tyr Gln Leu Leu Gln Ala Ser Leu Thr Cys Ser Pro His Arg Gln Arg
    50                  55                  60

Arg His His His His His His
65                  70

<210> SEQ ID NO 8
<211> LENGTH: 430
<212> TYPE: PRT
<213> ORGANISM: Chikungunya virus

<400> SEQUENCE: 8

Met Ser Thr Lys Asp Asn Phe Asn Val Tyr Lys Ala Thr Arg Pro Tyr
1               5                   10                  15

Leu Ala His Cys Pro Asp Cys Gly Glu Gly His Ser Cys His Ser Pro
            20                  25                  30

Val Ala Leu Glu Arg Ile Arg Asn Glu Ala Thr Asp Gly Thr Leu Lys
        35                  40                  45

Ile Gln Val Ser Leu Gln Ile Gly Ile Lys Thr Asp Asp Ser His Asp
    50                  55                  60

Trp Thr Lys Leu Arg Tyr Met Asp Asn His Met Pro Ala Asp Ala Glu
65                  70                  75                  80

Arg Ala Gly Leu Phe Val Arg Thr Ser Ala Pro Cys Thr Ile Thr Gly
            85                  90                  95

Thr Met Gly His Phe Ile Leu Ala Arg Cys Pro Lys Gly Glu Thr Leu
            100                 105                 110

Thr Val Gly Phe Thr Asp Ser Arg Lys Ile Ser His Ser Cys Thr His
        115                 120                 125

Pro Phe His His Asp Pro Pro Val Ile Gly Arg Glu Lys Phe His Ser
    130                 135                 140

Arg Pro Gln His Gly Lys Glu Leu Pro Cys Ser Thr Tyr Val Gln Ser
145                 150                 155                 160

Thr Ala Ala Thr Thr Glu Glu Ile Glu Val His Met Pro Pro Asp Thr
            165                 170                 175
```

```
Pro Asp Arg Thr Leu Met Ser Gln Gln Ser Gly Asn Val Lys Ile Thr
            180                 185                 190

Val Asn Gly Gln Thr Val Arg Tyr Lys Cys Asn Cys Gly Gly Ser Asn
        195                 200                 205

Glu Gly Leu Thr Thr Thr Asp Lys Val Ile Asn Asn Cys Lys Val Asp
    210                 215                 220

Gln Cys His Ala Ala Val Thr Asn His Lys Lys Trp Gln Tyr Asn Ser
225                 230                 235                 240

Pro Leu Val Pro Arg Asn Ala Glu Leu Gly Asp Arg Lys Gly Lys Ile
                245                 250                 255

His Ile Pro Phe Pro Leu Ala Asn Val Thr Cys Arg Val Pro Lys Ala
            260                 265                 270

Arg Asn Pro Thr Val Thr Tyr Gly Lys Asn Gln Val Ile Met Leu Leu
        275                 280                 285

Tyr Pro Asp His Pro Thr Leu Leu Ser Tyr Arg Asn Met Gly Glu Glu
    290                 295                 300

Pro Asn Tyr Gln Glu Glu Trp Val Met His Lys Lys Glu Val Val Leu
305                 310                 315                 320

Thr Val Pro Thr Glu Gly Leu Glu Val Thr Trp Gly Asn Asn Glu Pro
                325                 330                 335

Tyr Lys Tyr Trp Pro Gln Leu Ser Thr Asn Gly Thr Ala His Gly His
            340                 345                 350

Pro His Glu Ile Ile Leu Tyr Tyr Tyr Glu Leu Tyr Pro Thr Met Thr
        355                 360                 365

Val Val Val Val Ser Val Ala Thr Phe Ile Leu Leu Ser Met Val Gly
    370                 375                 380

Met Ala Ala Gly Met Cys Met Cys Ala Arg Arg Arg Cys Ile Thr Pro
385                 390                 395                 400

Tyr Glu Leu Thr Pro Gly Ala Thr Val Pro Phe Leu Leu Ser Leu Ile
                405                 410                 415

Cys Cys Ile Arg Thr Ala Lys Ala His His His His His His
            420                 425                 430
```

<210> SEQ ID NO 9
<211> LENGTH: 68
<212> TYPE: PRT
<213> ORGANISM: Chikungunya virus

<400> SEQUENCE: 9

```
Met Ala Thr Tyr Gln Glu Ala Ala Ile Tyr Leu Trp Asn Glu Gln Gln
1               5                   10                  15

Pro Leu Phe Trp Leu Gln Ala Leu Ile Pro Leu Ala Ala Leu Ile Val
            20                  25                  30

Leu Cys Asn Cys Leu Arg Leu Leu Pro Cys Cys Cys Lys Thr Leu Ala
        35                  40                  45

Phe Leu Ala Val Met Ser Val Gly Ala His Thr Val Ser Ala His His
    50                  55                  60

His His His His
65
```

<210> SEQ ID NO 10
<211> LENGTH: 446
<212> TYPE: PRT
<213> ORGANISM: Chikungunya virus

<400> SEQUENCE: 10

```
Met Tyr Glu His Val Thr Val Ile Pro Asn Thr Val Gly Val Pro Tyr
 1               5                  10                 15

Lys Thr Leu Val Asn Arg Pro Gly Tyr Ser Pro Met Val Leu Glu Met
             20                  25                 30

Glu Leu Leu Ser Val Thr Leu Glu Pro Thr Leu Ser Leu Asp Tyr Ile
         35                  40                  45

Thr Cys Glu Tyr Lys Thr Val Ile Pro Ser Pro Tyr Val Lys Cys Cys
     50                  55                  60

Gly Thr Ala Glu Cys Lys Asp Lys Asn Leu Pro Asp Tyr Ser Cys Arg
 65                  70                  75                  80

Val Phe Thr Gly Val Tyr Pro Phe Met Trp Gly Gly Ala Tyr Cys Phe
                 85                  90                  95

Cys Asp Ala Glu Asn Thr Gln Leu Ser Glu Ala His Val Glu Lys Ser
             100                 105                 110

Glu Ser Cys Lys Thr Glu Phe Ala Ser Ala Tyr Arg Ala His Thr Ala
         115                 120                 125

Ser Ala Ser Ala Lys Leu Arg Val Leu Tyr Gln Gly Asn Asn Ile Thr
     130                 135                 140

Val Thr Ala Tyr Ala Asn Gly Asp His Ala Val Thr Val Lys Asp Ala
145                 150                 155                 160

Lys Phe Ile Val Gly Pro Met Ser Ser Ala Trp Thr Pro Phe Asp Asn
                 165                 170                 175

Lys Ile Val Val Tyr Lys Gly Asp Val Tyr Asn Met Asp Tyr Pro Pro
             180                 185                 190

Phe Gly Ala Gly Arg Pro Gly Gln Phe Gly Asp Ile Gln Ser Arg Thr
         195                 200                 205

Pro Glu Ser Lys Asp Val Tyr Ala Asn Thr Gln Leu Val Leu Gln Arg
     210                 215                 220

Pro Ala Ala Gly Thr Val His Val Pro Tyr Ser Gln Ala Pro Ser Gly
225                 230                 235                 240

Phe Lys Tyr Trp Leu Lys Glu Arg Gly Ala Ser Leu Gln His Thr Ala
                 245                 250                 255

Pro Phe Gly Cys Gln Ile Ala Thr Asn Pro Val Arg Ala Val Asn Cys
             260                 265                 270

Ala Val Gly Asn Met Pro Ile Ser Ile Asp Ile Pro Glu Ala Ala Phe
         275                 280                 285

Thr Arg Val Val Asp Ala Pro Ser Leu Thr Asp Met Ser Cys Glu Val
     290                 295                 300

Pro Ala Cys Thr His Ser Ser Asp Phe Gly Gly Val Ala Ile Ile Lys
305                 310                 315                 320

Tyr Ala Ala Ser Lys Lys Gly Lys Cys Ala Val His Ser Met Thr Asn
                 325                 330                 335

Ala Val Thr Ile Arg Glu Ala Glu Ile Glu Val Glu Gly Asn Ser Gln
             340                 345                 350

Leu Gln Ile Ser Phe Ser Thr Ala Leu Ala Ser Ala Glu Phe Arg Val
         355                 360                 365

Gln Val Cys Ser Thr Gln Val His Cys Ala Ala Glu Cys His Pro Pro
     370                 375                 380

Lys Asp His Ile Val Asn Tyr Pro Ala Ser His Thr Thr Leu Gly Val
385                 390                 395                 400

Gln Asp Ile Ser Ala Thr Ala Met Ser Trp Val Gln Lys Ile Thr Gly
                 405                 410                 415

Gly Val Gly Leu Val Val Ala Val Ala Ala Leu Ile Leu Ile Val Val
```

```
            420                 425                 430
Leu Cys Val Ser Phe Ser Arg His His His His His His
        435                 440                 445
```

<210> SEQ ID NO 11
<211> LENGTH: 22
<212> TYPE: DNA
<213> ORGANISM: Artificial sequence
<220> FEATURE:
<223> OTHER INFORMATION: CHK SP FP1 PCR PRIMER

<400> SEQUENCE: 11
ctaaataggt acgcactaca gc                                              22

<210> SEQ ID NO 12
<211> LENGTH: 21
<212> TYPE: DNA
<213> ORGANISM: Artificial sequence
<220> FEATURE:
<223> OTHER INFORMATION: CHK SP FP2 PCR PRIMER

<400> SEQUENCE: 12
tggactccgc gccctactat c                                               21

<210> SEQ ID NO 13
<211> LENGTH: 20
<212> TYPE: DNA
<213> ORGANISM: Artificial sequence
<220> FEATURE:
<223> OTHER INFORMATION: CHK SP FP3 PCR PRIMER

<400> SEQUENCE: 13
tactcaggag gccggttcac                                                 20

<210> SEQ ID NO 14
<211> LENGTH: 17
<212> TYPE: DNA
<213> ORGANISM: Artificial sequence
<220> FEATURE:
<223> OTHER INFORMATION: CHK SP RP4 PCR PRIMER

<400> SEQUENCE: 14
gtgtcccatt gttccag                                                    17

<210> SEQ ID NO 15
<211> LENGTH: 20
<212> TYPE: DNA
<213> ORGANISM: Artificial sequence
<220> FEATURE:
<223> OTHER INFORMATION: CHK SP RP5 PCR PRIMER

<400> SEQUENCE: 15
gtgaaccggc ctcctgagta                                                 20

<210> SEQ ID NO 16
<211> LENGTH: 35
<212> TYPE: DNA
<213> ORGANISM: Artificial sequence
<220> FEATURE:
<223> OTHER INFORMATION: CHKCKOZAKFP PCR PRIMER

<400> SEQUENCE: 16
attgaattca ccatggagtt catcccaacc caaac                                35

<210> SEQ ID NO 17

```
<211> LENGTH: 39
<212> TYPE: DNA
<213> ORGANISM: Artificial sequence
<220> FEATURE:
<223> OTHER INFORMATION: CHKE1RP2 PCR PRIMER

<400> SEQUENCE: 17
aacaagcttg cggccgctta gtgcctgctg aacgacacg                              39

<210> SEQ ID NO 18
<211> LENGTH: 35
<212> TYPE: DNA
<213> ORGANISM: Artificial sequence
<220> FEATURE:
<223> OTHER INFORMATION: CHKSPE3FP PCR PRIMER

<400> SEQUENCE: 18
accgaattca tatgagtctt gccatcccag ttatg                                  35

<210> SEQ ID NO 19
<211> LENGTH: 38
<212> TYPE: DNA
<213> ORGANISM: Artificial sequence
<220> FEATURE:
<223> OTHER INFORMATION: CHKSPE3RP PCR PRIMER

<400> SEQUENCE: 19
tgcaagcttg gatccttagc gtcgctggcg gtggggag                               38

<210> SEQ ID NO 20
<211> LENGTH: 35
<212> TYPE: DNA
<213> ORGANISM: Artificial sequence
<220> FEATURE:
<223> OTHER INFORMATION: CHKSP6KFP PCR PRIMER

<400> SEQUENCE: 20
acggaattca tatggccaca taccaagagg ctgcg                                  35

<210> SEQ ID NO 21
<211> LENGTH: 38
<212> TYPE: DNA
<213> ORGANISM: Artificial sequence
<220> FEATURE:
<223> OTHER INFORMATION: CHKSP6KRP PCR PRIMER

<400> SEQUENCE: 21
attaagcttg gatccttagg tgcccacact gtgagcgc                               38

<210> SEQ ID NO 22
<211> LENGTH: 34
<212> TYPE: DNA
<213> ORGANISM: Artificial sequence
<220> FEATURE:
<223> OTHER INFORMATION: CHKCPFP PCR PRIMER

<400> SEQUENCE: 22
acagaattca tatggagttc atcccaaccc aaac                                   34

<210> SEQ ID NO 23
<211> LENGTH: 40
<212> TYPE: DNA
<213> ORGANISM: Artificial sequence
<220> FEATURE:
<223> OTHER INFORMATION: CHKCPRP PCR PRIMER

<400> SEQUENCE: 23
```

```
attaagcttg gatccttacc actcttcggc cccctcgggg                        40

<210> SEQ ID NO 24
<211> LENGTH: 35
<212> TYPE: DNA
<213> ORGANISM: Artificial sequence
<220> FEATURE:
<223> OTHER INFORMATION: CHKE1FP PCR PRIMER

<400> SEQUENCE: 24
tagaattcat atgtacgaac acgtaacagt gatcc                             35

<210> SEQ ID NO 25
<211> LENGTH: 38
<212> TYPE: DNA
<213> ORGANISM: Artificial sequence
<220> FEATURE:
<223> OTHER INFORMATION: CHKE1RP PCR PRIMER

<400> SEQUENCE: 25
tataagcttg gatccttagt gcctgctgaa cgacacgc                          38

<210> SEQ ID NO 26
<211> LENGTH: 38
<212> TYPE: DNA
<213> ORGANISM: Artificial sequence
<220> FEATURE:
<223> OTHER INFORMATION: CHKE2FP PCR PRIMER

<400> SEQUENCE: 26
tcggaattca tatgagcacc aaggacaact tcaatgtc                          38

<210> SEQ ID NO 27
<211> LENGTH: 41
<212> TYPE: DNA
<213> ORGANISM: Artificial sequence
<220> FEATURE:
<223> OTHER INFORMATION: CHKE2RP PCR PRIMER

<400> SEQUENCE: 27
tccaagcttg gatccttacg ctttagctgt tctgatgcag c                      41
```

VACCINE FOR CHIKUNGUNYA VIRUS INFECTION

FIELD OF THE INVENTION

The present invention relates to vaccine formulation capable of eliciting protective immune response against Chikungunya virus (CHIKV) infection in humans and other mammalian hosts. The immunogenic formulation comprises purified inactivated Chikungunya virus in a stable formulation. The method of adaptation and propagation of the virus in vitro in continuous cell culture in vaccine quality cell lines such as Vero and MRC-5 cells that are approved by FDA/National Regulatory Authority is provided. Purification and methods of inactivation of the virus are discussed. The method of preparation and administration of liquid and lyophilized formulations of the virus with added stabilizers is discussed. The inactivated virus preparation is non-infectious, immunogenic and elicits protective immune response in mammalian host. The immunogenic composition is formulated for in vivo administration to humans. Within the scope of the present invention is the strategy of developing a subunit vaccine using the recombinant virus proteins as antigens capable of eliciting protective immune response against Chikungunya virus infection in mammalian hosts. The recombinant antigens could potentially find use in diagnosing for the presence of the virus.

BACKGROUND OF THE INVENTION

Disease and epidemiology: Chikungunya is a physically debilitating disease of humans mainly in Africa and Asia. The symptoms include abrupt onset of high fever, rash or hemorrhages, arthralgia and occasional involvement of the nervous system, heart and liver. The incapacitation is due to arthralgia, which can persist for years (Sarkar et al., 1965; Rao et al., 1965; Nimmannitya et al., 1969; Schuffenecker et al., 2006). The disease is caused by Chikungunya virus (CHIKV), and is spread by *Aedes* spp. mosquitoes, either through other forest-dwelling vertebrate hosts (in Africa) or by a human-mosquito-human cycle (in Asia) (Powers et al., 2000). There have been several major outbreaks of the disease, including the recent ones in the Indian Ocean, Malaysia and India, with several thousands of people afflicted. In India, the major outbreaks appear to have occurred once in the 1960s and then in 2005-2006 (Shah et al., 1964; Rao et al., 1965; Chaturvedi et al., 1970; Ravi, 2006). In the recent outbreak, several districts in Karnataka, Andhra Pradesh, Tamil Nadu, Maharashtra, and possibly Orissa have been affected. The disease can be diagnosed by various serological tests, but definitive identification requires verification of the genetic material since many closely related arboviruses cause similar disease. Treatment is only palliative and there is no commercially available vaccine.

The virus harbors a single-stranded, positive sense RNA genome, and belongs to group A arboviruses along with Sindbis and Semliki Forest disease viruses in the alphavirus genus of Togaviridae family (Fauquet et al., 2005). The virion is 50-60 nm in size and is inactivated by 70% ethanol, 1% sodium hypochlorite, 2% glutaraldehyde, lipid solvents, moist or dry heat >58° C., as well as drying.

Genotyping suggests the existence of three clades: West African, East-Central-South-African and Asian. The Asian and African strains form closely-related clades that differ from each other in sequence, antigenicity and virus properties. The Asian isolates appear to be more conserved than either of the African clades (Powers et al., 2000; Schuffe-necker et al., 2006). The recent Indian Ocean outbreak isolates show a characteristic change from Alanine to Valine in position 226 of the envelope glycopriten E1 from early to later phase of the disease, respectively (Schuffenecker et al., 2006). While the importance of this is not understood, an evolutionary advantage for the virus can be surmised.

Not much is known about the viral proteins, their function or pathogenicity. The genome consists of ~12 kilobases, with a 5' 7 mG cap and the 3' poly(A) region, and a base composition of 30% A, 25% C and G, and 20% U. The genome has the sequence of 5'-nsP1-nsP2-nsP3-nsP4-(junction region)-C-E3-E2-6K-E1-polyA-3'. The non-structural proteins are translated directly from the 5' two-thirds of the genome, and the structural proteins are produced from the 26S subgenomic RNA which is collinear with the 3' one-third of the genome. The genome contains conserved repeat sequences as well as an internal poly(A) tract within the 3' non-translated region (Khan et al., 2002; Schuffenecker et al., 2006).

Based on sequence information, it has been deduced that nsP1, nsP2, nsP3, nsP4, C, E3, E2, 6K and E1 proteins contain 535, 798, 530, 611, 261, 64, 423 and 61 amino acids (Khan et al., 2002; Schuffenecker et al., 2006). The envelope proteins can be observed on SDS gels as 62 kD E2/E3, which is cleaved into E2 and E3 within 90 mins, and 45-50 kD E1 and E2 that migrate closely together. E1 and E2 associate tightly with each other rapidly. The 11 kD E3 protein is not associated with the virion, and is released into the medium (Simizu et al., 1984; Ranadive and Banerjee, 1990). The viral E1 glycoprotein agglutinates erythrocytes, and hemagglutination (HA) and hemagglutination inhibition (HI) tests can be performed routinely on goose erythrocytes for diagnostic purposes. HA activity of the virus is not susceptible to trypsin, and is enhanced by tween-ether treatment (Hannoun, 1968). Serum with HI titers of >40 generally shows neutralization capacity (Bedekar and Pavri, 1969b). Isolation of virus can be performed in newborn rats or mice, or in animal or insect cell cultures. Vero, African green monkey kidney, BHK21, BSC-1, chick embryo fibroblasts and C6/36 cells have been used for in vitro virus isolation and expansion. The virus replicates fairly rapidly in cell culture. Depending on dose and on the cell line, cytopathic effect can be observed in 12-48 hrs. At multiplicities of 1-5, following a 5-6 hr eclipse period, the intracellular virus titer rises sharply and reaches peak by 12 hrs. Extracellular virus can be observed at 8 hrs post-infection and peaks at 12-24 hrs depending on the cell system and dose of the inoculum (Chain et al., 1966; Higashi et al., 1967; Hahon and Hankins, 1970; Eckels et al., 1970). Spread of infection through the monolayer differs in different cell types, involving both extracellular and cell-to-cell transmission in BHK21 cells, but only the former in L929 and guinea pig lung cells (Hahon and Zimmerman, 1970). Titers in supernatants can reach as high as that observed with mouse brain preparations (Shah et al., 1964; Paul and Singh, 1968; Umrigar and Kadam, 1974).

The virus can be concentrated from cell culture supernatant by ultracentrifugation, or precipitation with ammonium sulphate, alum, or polyethylene glycol (Eckels et al., 1970; Klein et al., 1970; Banerjee and Ranadive, 1988; Killington et al., 1996). The virus can be further purified by using rate zonal centrifugation, equilibrium density gradient or gel filtration (Eckels et al., 1970; Simizu et al., 1984; Banerjee and Ranadive, 1988). Titration of the virus can be performed by immunofluorescence, ELISA, complement fixation, agar gel immunodiffusion, hemagglutination and inhibition, plaque assays, or neutralization.

It is unknown how CHIKV or other alphaviruses cause arthritis. Suggested mechanisms include replication leading to cell death and tissue damage, immune-mediated attack on the joints, or immune-complex-mediated inflammation. While Semliki forest virus and Ross River virus have been shown to known to replicate in bone-associated connective tissue in neonates as well as skin and muscle in adult mice (Heise et al., 2000), no such study has been done with CHIKV.

In contrast to Dengue virus, which requires adaptation for infection of animals, CHIKV shows rapid and high fatality on primary inoculation of clinical samples (Myers et al., 1965). However, newborn mice and rats are the only species that show disease (Chakravarthy and Sarkar, 1969). In a dose-dependent manner, rat/mouse pups show illness and high mortality following intracerebral, intraperitoneal or subcutaneous inoculation of patient sera in 3-10 days, yielding $10^{5.5}$-$10^{7.0}$ mouse-$LD_{50}$ of virus per mL of serum (Shah et al., 1964). Animals rapidly manifest sluggishness, severe inappetence, cyanosis, dermal hypothermia, and death. Pathologically, they show cardiac enlargement, hemorrhages in gastrointestinal tract, alveoli, bladder, joints and skin, skeletal muscle and fat pad necrosis, and diffuse intestinal dysfunction (Nimmannitya et al., 1969; Weiss et al., 1965). Survivors (injected lower doses) show stunted growth, but develop HI antibodies and are protected from challenge after intracerebral or intraperitoneal challenge (Shah et al., 1964; Giovarelli et al., 1977). Newborn bunnies and guinea pigs are moderately susceptible with some virus recovery, and one-day kitten are less susceptible. Adult mice, rats, guinea pigs, hamsters, hare and rabbits show viremia, but not disease, and develop HI and neutralizing antibodies, whereas adult cats and fowl don't. Low titers of HI antibodies without viremia or neutralizing antibodies can be seen in cows, sheep, goats and horses (McIntosh et al., 1963; Bedekar and Pavri, 1969a; Chakravarthy and Sarkar, 1969). The susceptibility of birds is controversial. In one study, white leghorn chicks have been shown to succumb to virus inoculation, and recovered birds develop neutralization antibodies (Bedekar and Pavri, 1969a). This and other studies involving chicken, sparrows, pigeons and bats have shown seroconversion without viremia or nothing (Shah et al., 1964; Bedekar and Pavri, 1969a).

Adult monkeys belonging to various species show viremia, can transmit virus to mosquitoes, and develop long lasting neutralizing antibodies (Paul and Singh, 1968). Wild monkeys and baboons in Africa circulate high titres of the virus without any apparent sickness as a result of infection, and can transmit the virus to through mosquitoes (McIntosh et al., 1963). However, serological evidence of natural infection of monkeys does not exist in India (Bedekar and Pavri, 1969b).

CHIKV infection (whether clinical or silent) is thought to confer life-long immunity. Because of close antigenic relationship, cross-protection between different strains (Casals, 1957; Porterfield, 1961; Shah et al., 1964) as well as reciprocal cross-protection among other alphaviruses (Parks and Price, 1958; Hearn and Rainey, 1963) can be hypothesized, and is demonstrated in animal models. However, there is some evidence that live attenuated alphavirus vaccines may interfere with a subsequent, related vaccine (McClain et al., 1998).

As a prelude to vaccines, initial CHIKV preparations involved either formalin inactivation (Harrison et al., 1967) or tween-ether extraction of virus grown in vitro (Eckels et al., 1970). While formalin kills HA activity, the latter treatment retains the HA activity completely, although both lose infectivity drastically. However, they both elicit similar HA and complement-fixing and neutralization antibodies and also show similar levels of protection in lethal challenge studies (Eckels et al., 1970).

US Army Medical Institute of Infectious Diseases in Fort Detrick, Md. made a candidate vaccine for CHIKV. CHIKV strain 15561 from Thailand (1962 outbreak) was used to develop a small lot of green monkey passaged, formalin-inactivated preparation that was administered to 16 volunteers who showed high immune responses and no adverse effects (Harrison et al., 1971). The GMK-passaged virus was further serially passaged by plaquing 18 times in MRC-5 cells (Levitt et al., 1986), and found to be safe and immunogenic in phase I trial with 15 alphavirus-naïve individuals, viremia occurring on day 2-4 post-inoculation (McClain et al., 1988). In a randomized, double-blind, placebo-controlled, phase II trial, 73 alphavirus-naïve volunteers of 18-40 years were injected with 0.5 mL dose containing either ~$10^5$ PFU of virus (59 subjects) or placebo (14 subjects) subcutaneously. Serological evaluation involved plaque reduction neutralization titer (PRNT), and a 50% reduction titer of ≥20 was considered positive. Local and systemic reactions were limited to vaccine take whereas 8% of CHIKV vaccinees (and none of placebo group) showed arthralgia. 98.3% of vaccinates seroconverted by day 28, achieving peak $PRNT_{50}$ titers of 1:10240 at 28-42 days. Although antibody levels declined somewhat over time, 85% of the vaccinees were still seropositive at one year, with titers of 1:1280 at 180-360 days (Edelman et al., 2000).

Panel A—Lane 1—Capsid PCR product; Lane 2-100 bp ladder; Lane 3—E2 PCR product

Panel B—Lane 1—E1 PCR product; Lane 2 —1 Kb ladder

Panel C—Lane 1-100 bp ladder; Lane 2—E3 PCR product

Figure 8:
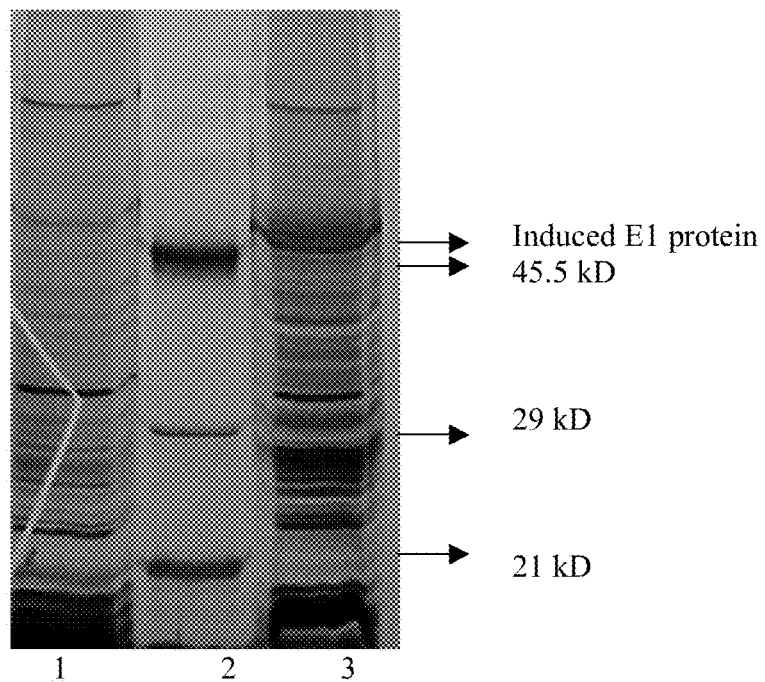

FIG. 8 SDS-PAGE of induction of cloned E1 protein in *E. coli* expressed cells. Lane 1—uninduced cells; Lane 2—protein molecular size marker; Lane 3—*E. coli* cells 4 hours after induction with IPTG showing the induction of ~47 kD E1 protein.

Figure 9:
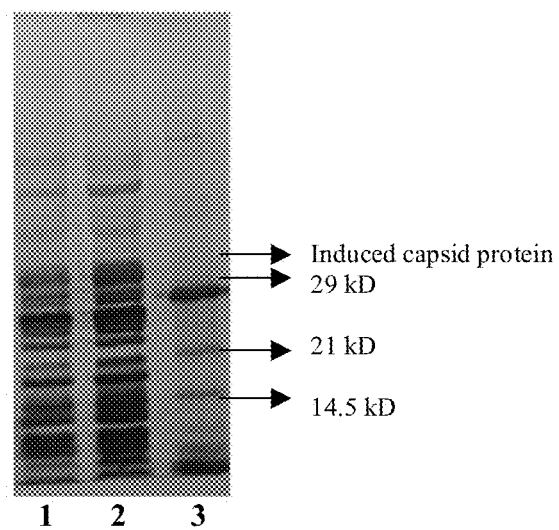

FIG. 9 SDS-PAGE of the induced ~30 kD Capsid protein in *Pichia pastoris*; Lane 1—protein expression at 0 hours after induction with methanol; Lane 2—at 72 hours after induction with methanol; Lane 3—protein molecular size marker.

SUMMARY OF THE INVENTION

The scope of the present invention includes the procedure for isolation of Chikungunya (CHIK) virus from infected human serum samples, methods for adaptation and propagation of the virus in a continuous culture to a high titer in an FDA/National Regulatory Approved cell lines such as Vero and MRC-5 and harvesting the virus from the infected cells in culture. The methods described in the present invention are applicable to any genotype/strains/genetic variants of Chikungunya virus and is known to those skilled in the art. The scope of the current invention includes methods used for the purification of the virus from the infected cells substantially free of cellular and serum components. One of the methods used in the current invention includes the use of proprietary Himax™ technology for purification of the virus. The purified virus is inactivated either by heat or chemically inactivated with one of the inactivating agents that includes but is not limited to the following agents: formalin, beta-propiolactone, glutaraldehye, non-ionic detergents, ascorbic acid etc. The vaccine formulation comprises a pharmaceutically accepted buffer such as phosphate or phosphate-citrate buffer in the pH range 6.4-7.5 with added stabilizing agents that includes one or more of the following but is not limited to: human serum albumin, gelatin, reducing and non-reducing sugars, amino acids, polyols such as sorbitol and mannitol, glycerol organic and inorganic salts, polyvinyl pyrrolidone etc. The stable formulation in a liquid form is suitable for intramuscular/intradermal/subcutaneous/intravenous administration in a human host. The stable formulation in a dry lyophilized form can be reconstituted with a suitable solvent before administration. The formulations are suitable for oral and intranasal administration in humans. The efficacy of the vaccine formulation has been established by various methods such as virus neutralization test and hemagglutination inhibition assay. The estimation of the antigenic protein is by using standard protein estimation methods and by ELISA. Potency of the vaccine has been tested in animal models. The potency of the vaccine formulation has been tested in doses ranging from 1 μg upto 200 μg of the antigen where the inactivated virus is the active ingredient in the formulation. A high rate of seroconversion and protective antibodies against the virus has been observed in rabbits that have been administered the formulation.

The adaptation and growth of the virus in a continuous cell culture in a cell line such as Vero/MRC-5 that is approved by FDA and National Regulatory Authorities offers an affordable, reproducible and an easy to be validated method of propagation of Chikungunya virus in continuous cell culture suitable in industrial scale production of a stable formulation of the virus that can be used as a vaccine. The stable formulation of the inactivated Chikungunya virus with added stabilizers is immunogenic eliciting protective immune response against Chikungunya virus strains.

The present invention also describes a strategy for developing a subunit vaccine using recombinant virus proteins as antigens. The viral proteins can be expressed as recombinant proteins either in prokaryotic or eukaryotic host cells. As known to those skilled in the art, the methods of cloning and expression described herein are applicable to any genetic variants/mutants of the virus proteins.

DETAILED DESCRIPTION OF THE INVENTION

The properties of the Chikungunya virus particles as an immunogen, adaptation and propagation of the virus in host cell lines to a high titer, determination of the identity of the virus by RT-PCR, electron microscopy; methods of purification and inactivation of the virus, preparation of stable liquid and lyophilized vaccine formulation(s) in a pharmaceutically acceptable carrier suitable for administration in human, viral methods and tests for vaccine potency in animal model have been discussed.

The active ingredient or immunogen, of the vaccine described in the current invention is inactivated virus particles of Chikungunya virus. The methods described in the current invention are applicable to any genotype/strains of Chikungunya virus. The virus particles obtained from the clinical isolates from patients' serum have been adapted and propagated in vitro in cell monolayers for several passages. In alternative protocol, the virus particles have been passaged once through 2 day old suckling mice and the virus re-isolated and passaged in cell monolayers in vitro.

The Chikungunya (CHIK) virus vaccine according to the present invention refers to an active ingredient (immunogen) of an inactivated Chikungunya virus that is produced under cGMP conditions by infecting in a monolayer of Vero cells or MRC-5 cells in continuous cell culture where the cells are used as host cells for culturing the Chikungunya virus. The cell line is qualified through various quality control tests and is approved by FDA/National Regulatory Authority as a vaccine quality cell line. The virus is propagated in large quantities by growing to a high titer (~$10^9$) in cell culture and purified from infected cells. The virus is inactivated either by heat or with an inactivating agent.

A neutralizing antibody titer of the anti-serum obtained by immunization with the above particles in a stable formulation, as measured by in vitro neutralization assay offers protective immunization in animals.

The immunogen of a Chikungunya virus vaccine is a representative example of an immunogen of a vaccine against infectious diseases caused by Chikungunya viruses of any strain or genotypic variants of the Chikungunya virus. The vaccine of the present invention is provided in a sealed vial or ampoule in a liquid or lyophilized form. In the case of liquid formulation, it can either be subcutaneously/intramuscularly/intradermally/intravenously injected or orally/intranasally administered to a subject to be vaccinated in an amount of about 0.05 ml to 5 ml per person. In the case of a dry lyophilized formulation, it is injected after being re-solubilized with a suitable solubilizing solution.

According to the present invention, the method that is applicable to strains of Chikungunya virus being used in the current invention is applicable to any Chikungunya virus strain with a broad antigenic spectrum. The broad spectrum antigenic response would offer a satisfactory immune protection against plural strains of CHIK virus in addition to the virus strain used in production of the vaccine. As known to those skilled in the art, a divalent or polyvalent vaccine may be prepared by mixing vaccines produced from two or more CHIK virus strains that have been genetically confirmed as CHIK viruses and is mixed in a suitable ratio based on the antigenic protein content. Such mixing would provide a vaccine preparation having a broader antigenic spectrum for protection against the infection.

According to the current invention, inoculating an appropriate host cell line such as Vero cells/MRC-5 cells with the virus, and maintaining the infected cells in continuous culture A culturing method involves infecting the host cell monolayer with the virus and harvesting the virus in sufficient quantities from the infected host cells. The virus grown in cell layers could include a population of the extracellular virus that is obtained in the supernatant of the infected cell culture that can be harvested by centrifugation, and harvesting the virus that is cell associated by sonication and centrifugation.

A cell line that can be propagated in vitro in culture can be used as a host for virus culture. For example, diploid cell lines such as MRC-5 and WI-38 and serially passaged cell lines such as Vero, BHK-21, CHO cells etc. can be used. For propagating Chikungunya virus strains, preferably permissive cells are selected which allow the virus to grow well. For example Vero (ATCC No. CCL-81), BHK-21 (ATCC No. CCL-10), C6/C3 (ATCC No. CRL-1660) etc. are preferably used. One such cell line used in the current invention is Vero cells which have been validated for use as a host cell for vaccine production. The validated Vero cell lines conforms to the Requirements for Biological Substances No. 50 regarding requirements for use of cells for the production of biologicals recommended by the World Health Organization (WHO) thereby confirming these cell lines as qualified for producing a vaccine (WHO Technical report Series, No. 878, pp 19-52, 1998). Furthermore CV-1, BSC-1, MA104, MDCK, CaCO-2 etch and DBS-FLC-1, DBS-FLC-2, DBS-FRh1-2, ESK-4, HEL, IMR-90, WRL68, etc. conventionally used for producing a virus vaccine can also be used ("ATCC Microbes and Cell at Work", $2^{nd}$ Edition., pp 144, American Type Culture Collection (ATCC) 1991, USA).

For maintenance in cell culture of the above-mentioned cell lines, stationary culture in monolayers, perfusion system culture, shake flasks, roller tube/bottle culture, suspension culture, microcarrier culture, cell factories and cell stacks and the like can be adopted. For example commercially available Cytodex (Pharmacia Biotech, Sweden) of various types are used as a microcarrier, and other commercially available animal cell culture devices can be used.

An inactivating agent such as formalin, beta-propiolactone, and glutaraldehyde is added to a virus suspension to inactivate the virus. For example when using formalin and beta-propiolactone, the amount to be added is about 0.001% to 0.4% (v/v), the inactivation temperature is about 2-8 DEG C to about 40 DEG C and the inactivation duration mainly depends upon the inactivation temperature. For e.g. it could range between 2 hours to 72 hours at 37 DEG C and about 12 hours to 250 hours at 2-8 DEG C. Inactivation is also effective at intermediate temperatures of around 22 DEG C for a period of 2-120 hours. Inactivation of the virus can also be carried out by non-ionic detergents and ascorbic acid. Heat inactivation is effective for Chikungunya virus at temperatures at around 56-58 DEG C for one hour.

Purification of the virus is conducted by physical means or chemical means and preferably by a combination of both. Physical methods utilize the physical properties of the virus such as density, size, mass, sedimentation coefficient etc. and includes any of the following techniques but is not limited to: zonal ultra-centrifugation, density gradient centrifugation, ultrafiltration with membranes with size cut offs ranging from 50-1000 kDa to remove serum and cellular components. Purification through chemical means employs methods such as adsorption/desorption through chemical or physiochemical reactions and includes for example purification by ultracentrifugation, density gradient centrifugation, ion exchange chromatography, affinity chromatography, hydrophobic interaction chromatography, gel filtration chromatography, salting with inorganic salts one such example being ammonium sulphate, and by the use of proprietary Himax™ technology, organic salts, organic solvents, aluminium phosphate, aluminium hydroxide and organic compounds such as polyethylene glycol. Purification of the virus is achieved by either one or a combination of two or more of the above mentioned methods.

Concentration of the virus is achieved by low-speed centrifugation with ultrafiltration membrane, precipitation with salts or purification with Himax™ Technology Inactivation of the virus particles can be achieved either before or after purification of the virus.

The virus can be visualized by a negative staining method using 2% (w/v) uranyl acetate can be observed under an electron microscope at a magnification of about 20,000 to about 200,000.

The genetic identity of the CHIK virus was confirmed by sequencing the cDNA complementary to the genomic RNA of the strains. More specifically, genomic RNA was extracted from virus infected cells or from the purified CHIKV after pelleting by ultracentrifugation or isolation on a density gradient. Thereafter, a region encoding an envelope protein or non-structural protein was further amplified by reverse transcriptase polymerase chain reaction (RT-PCR) using a pair of primers and the base sequence of the resultant cDNA is determined by dideoxy chain termination method.

The amino acid sequence encoded by the base sequence was decoded using universal codes and the genetic identity of the virus was confirmed as Chikungunya virus.

An inactivated virus particle of the present invention is diluted with any suitable diluent that is pharmaceutically acceptable so as to obtain the desired titer. The buffer used in the formulation may be phosphate or phosphate-citrate buffer. A vaccine may optionally contain preservative(s), stabilizer(s) etc. Reducing and non-reducing sugars, sugar alcohols such sorbitol and mannitol, glycerol, amino acids, human serum albumin is added in the range of 0.01% to 10% for the liquid formulation and upto 60% of the total solids for a lyophilized formulation. Such a stable formulation of the immunogen either in a liquid or in a lyophilized form and after reconstitution in a pharmaceutically acceptable buffer or water is suitable for administration intradermally/subcutaneously/intramuscularly/intravenously in human host and is also suitable for oral and intranasal administration.

The vaccine for Chikungunya virus alternatively could be a subunit vaccine prepared with the structural proteins such as, Capsid, E1 and E2 and E3 glycoproteins of the Chikungunya virus strains either cloned and expressed individually and purified for constituting a vaccine formulation, or by expressing the entire structural polyprotein consisting of the Capsid, E3, E2, 6K polypeptide and E1 proteins that is cloned as a single polypeptide with a potential to assemble into a Virus Like Particle (VLP) in eukaryotic host cells such as yeast, in insect cells via baculovirus mediated expression, and in mammalian cells after being processed by host signal peptidases. The VLPs are highly immunogenic as they mimic the native virus particle in structure when processed correctly for assembly by the host signal peptidases. They contain multiple copies of the antigenic proteins in their assembled structure. The viral proteins either expressed in prokaryotic or eukaryotic host cells are purified free of host cell proteins. The purified structural proteins can be administered in a formulation and by the methods described above. The addition of Histidine residues to either end of the recombinant proteins while cloning facilitates purification of the recombinant proteins.

In another aspect of the invention, virus particles obtained according to the present invention, as well the recombinant viral proteins can be used as a reagent (as an antigen) in the diagnostic tests e.g. as an antigen in an immunoprecipitation method, a hemagglutination inhibition (HI) test, complement fixation (CF) reaction, ELISA, radioimmunoassay, immunofluorescence, Western Blot and the like. More specifically using the entire or a part of an inactivated virus particle of the present invention, a diagnostic assay with high sensitivity and specificity for detecting infection by different strains of the Chikungunya virus can be provided. As used herein the term "a part" of an inactivated virus particle refers to a fraction of the virus which retains desired antigenicity and is derived from the virus particles including for example, structural protein solubilized during the purification step described in the given examples or expressed in a recombinant expression system. Polyclonal antibodies or monoclonal antibodies specific for the virus can be used in a diagnostic assay for Chikungunya virus infection.

For potency testing of the vaccine, the vaccine formulations were tested in Balb/c mice and rabbits. The animals in each group were injected intraperitoneally with about 0.2 to 0.5 ml/mouse of serially diluted vaccine preparation ranging in dose from 1 µg to about 500 µg for the different test groups. A booster dose was given 7-14 days after the first administration of the antigen. A formulation of the inactivated virus preparation formulated in aluminium hydroxide in combination with oligonucleotides gave a higher immune response. The resultant serum was assayed by in vitro neutralization tests and the antibody titer was determined by ELISA. Seroconversion was observed in the animals immunized with the vaccine formulation.

The following examples are included solely to aid in a more complete understanding of the invention described and claimed herein. The examples do not limit the scope of the claimed invention in any fashion it should not construe the scope of the protection of the claims. However, one of the ordinary skilled in the art appreciates the modifications and changes can be made without departing from the scope of the present invention as set forth in the claims below. The benefits, advantages, solutions to problems, and any element(s) that may cause any benefit, advantage, or a solution to occur or become more pronounced are not to be construed as critical, required, or essential features or elements of any or all the claims. The invention is defined solely by the appended claims including any amendments made during the dependency of this application and all equivalents of those claims as issued.

EXAMPLE 1

Proliferation in a cell line for virus culture: Vero cell line (ATCC No. CCL-81), BHK-21 cells and MRC-5 cells were used as candidate cell lines for Chikungunya virus (CHIKV) culture and good viral propagation in each cell line was observed. Vero cells and BHK-21 cells were each prepared in a growth medium consisting of DMEM (Dulbecco's Modified Eagle Medium; Sigma-Aldrich Catalog #D5523 and used per the manufacturer's instructions) containing 5% fetal bovine serum (FBS). They were statically incubated at 37° C. until reaching 80-100% confluence of the monolayer. Thereafter the number of cells was counted. MRC-5 cells were prepared in growth medium consisting of MEM (Minimal Eagle's Medium) buffered to neutral pH with Hepes buffer and consisting of 5% FBS, was statically incubated at 37° C. for 6 days and thereafter the cells were counted. In an alternate procedure, Vero cells and MRC-5 cells were cultured in serum free medium. For scaling the production of cells for virus infection, one cryo vial containing $5 \times 10^6$ viable Vero cells from working cell bank were used for seeding one T175 Cell culture grade flask. DMEM containing 5% FBS and 50 µg/ml of neomycin sulfate was used for revival and replenishing the cells. After 90% of the confluence of the cell monolayer in T175 flasks, the cells were trypsinized and propagated further in cell factories/cell stacks (CF 10). The same DMEM medium is used for propagation (~2.0 L/CF10).

EXAMPLE 2

Figure 1:
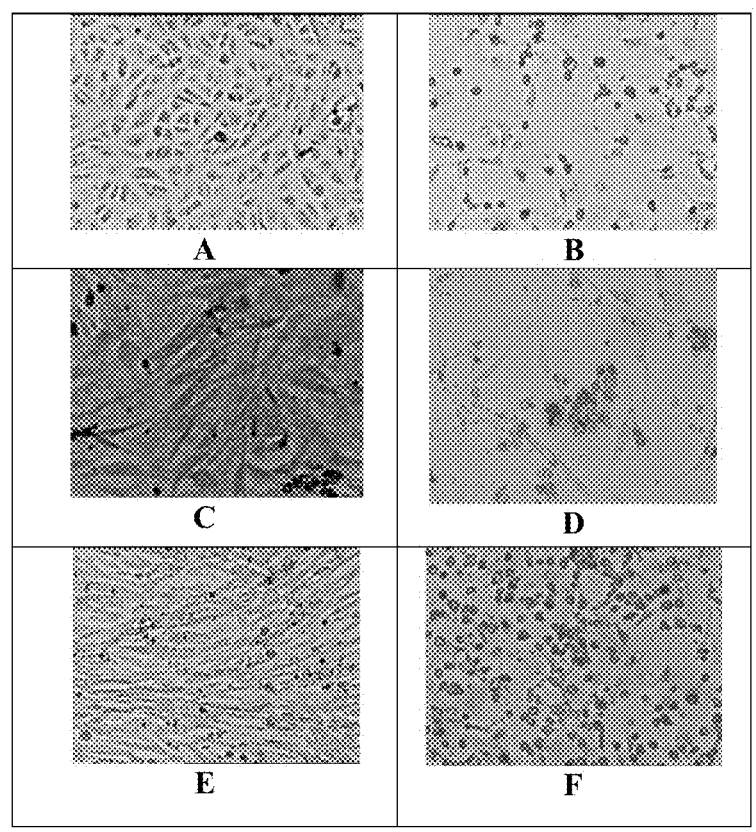
FIG. 1: A—Control uninfected Vero cells
B—CHIK infected Vero cells
C—Control MRC-5 cells
D—CHIKV infected MRC-5 Cells
E—BHK21 Control cells
F—CHIKV infected BHK21 cells

Isolation of the Virus:

Chikungunya virus (CHIKV) was isolated from serum of infected patients who had the classical clinical symptoms of Chikungunya virus infection. The Indian isolate(s) of the virus were used in the development of the vaccine formulation. Of the many isolates obtained, two isolates namely, CHK/03/06 and CHK/01/06 were characterized. The blood sample drawn from the patient was transported at 4° C. and the serum was separated. The serum was diluted 1:1 with phosphate buffered saline (PBS) and 0.5 ml of the diluted serum was used for infection of Vero cells (ATCC No. CCL-81) in $25^2$ cm flask and incubated at 34° C. to 37° C. in serum free medium. The control flask of Vero cells was treated with equal volume of 1×PBS. Post-infection, the medium for propagation of Vero cells was DMEM containing 1% fetal bovine serum (FBS) In an alternate method, the cell and virus culture were carried out in serum free medium. The virus was harvested 30-48 hours after infection. The cytopathic effect (cpe) of Chikungunya virus isolate CHK/03/06 in infected Vero cells was as observed in FIGS. 1 B, and 1A is the uninfected control. The virus was also cultured under similar conditions in MRC-5 cells and the cytopathic effect of CHK/03/06 observed in MRC-5 cells is depicted in FIG. 1D. 1C is the uninfected control MRC-5 cells. The cpe of the virus in BHK21 cells is observed in FIG. 1F and that of the control uninfected BHK-21 cells is depicted in FIG. 1E. In one of the alternate methods tried, Vero and MRC-5 cells were treated with chemical agents such as trypsin at low concentrations ranging from 0.01% to 1% and with or without divalent ions such as calcium and magnesium before infection.

EXAMPLE 3

Propagation of the CHK/01/06 and CHK/03/06 virus isolates: The CHK/01/06 and CHK/03/06 virus isolates were propagated in continuous cell culture in Vero cells (ATCC No. CCL-81) and in BHK-21 cells and MRC-5 cells. The medium for the infection was DMEM containing 0%-1% FBS. At the end of 48 hours of infection, the cytopathic effect was near total in Vero and BHK21 cells and the virus was present largely in the extracellular medium. A $TCID_{50}$ of the virus upto $10^9$/ml was obtained. The virus isolates were passaged serially 23 times in Vero cells and were found to be stable in continuous cell culture. The virus titer significantly enhanced after passaging through mouse brain. Virus infection and propagation were also alternately tested in a serum free medium.

EXAMPLE 4

Purification of the virus: The two virus isolates were purified from the infected Vero cell monolayers by methods that include but not is limited to: low-speed centrifugation to remove much of the cellular debris and serum components, ultracentrifugation, sucrose density gradient centrifugation, and ultrafiltration through 100-1000 kDa membrane. The virus was further purified by ion exchange column chromatography and by gel filtration in Sepharose CL 4B or a matrix of similar property. The fractions containing the virus were pooled and precipitated with salts that included one of the following: PEG in the presence of 0.020M-0.20 M NaCl, precipitation using Himax™ technology, ammonium sulphate, alum etc. The infectivity of the virions was checked by re-infection of the Vero, BHK 21 and MRC-5 cells and was found to be infectious. The concentrated virus was resuspended in phosphate buffer, pH 7.2 for checking in 7.5%-12% SDS-PAGE and virus proteins were visualized by silver staining. High purification of the virus was achieved also by ion exchange chromatography and hydrophobic interaction column chromatography and by the use of Monolith™ columns with salt elution. The purity of the virus preparation was checked by silver staining of SDS-PAGE gel and by Western blot using anti-CHIKV antisera raised in rabbit. Purification on the Monolith anion exchange columns gave a higher recovery of infectivity. Infectivity of the virus was also monitored during different steps of a pilot scale purification that eliminates serum and host cell contamination of the virus and $TCID_{50}$ of $10^5$ to $10^7$/ml could be routinely obtained and is being further optimized.

EXAMPLE 5

Figure 2:
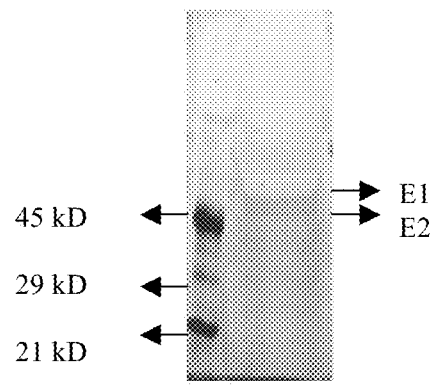
FIG. 2: SDS-PAGE of purified CHIKV preparation depicting the E1 and E2 proteins that appears to be more predominant than the virus antigens. The virus sample was run in 12% denaturing SDS-PAGE gel and visualized by silver staining. The two proteins appear to be approximately 46-50 kD in size.
Figure 3:
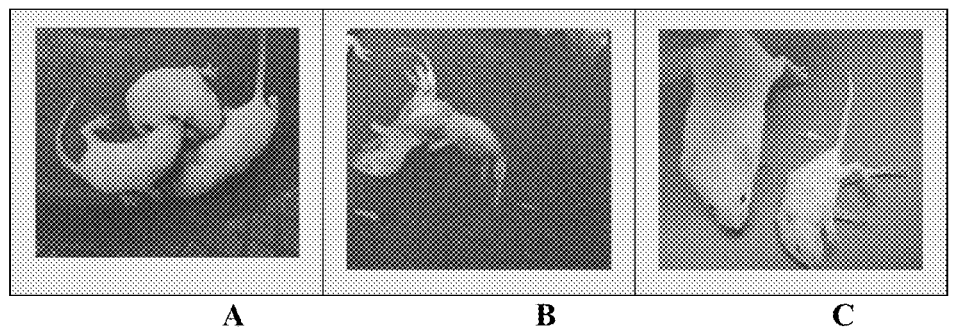
FIG. 3: In vivo toxicity of the purified Chikungunya virus isolate CHK/03/06 after intracerebral injection in mice. 2-day old mice were injected purified Chikungunya virus isolate CHK/03/06 intracerebrally and the control animals were injected with equal volume of PBS.
Panel A—control mice 7 days after injection of PBS
Panel B—mice injected with purified virus were found dead on the $6^{th}$ day after intracerebral injection of the purified virus preparation.
Panel C—On the $9^{th}$ day after intracerebral injection in 2-day old mice, the PBS injected control animal shows normal growth (left) and the mice injected with 1:64 dilution of the purified virus preparation shows severe growth retardation.

The purity of the virus preparation was checked by SDS-PAGE was found to be of good purity. The E1 and E2 envelope glycoproteins could be easily detected. See FIG. 2. The purified virus was had infectivity as determined by determining the infectious count of the virus and by intracerebral injection of the purified virus fraction in 2-day old mice, at various dilutions. Neat purified virus and several serial dilutions resulted in death when injected intracerebrally. The mice showed severe retarded growth when compared to PBS injected control mice as observed in FIG. 3

EXAMPLE 6

Figure 4:
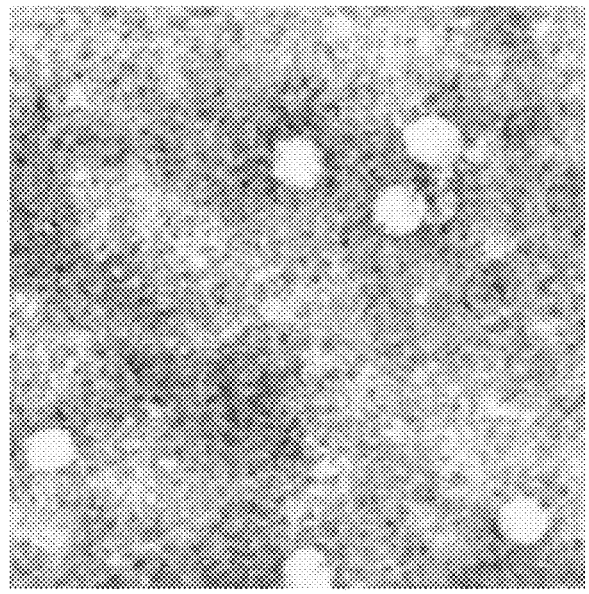
FIG. 4: Transmission Electron Micrograph (TEM) of the CHK/03/06 isolate at 200 K magnification FIG. 5 Ethidium bromide stained photograph of RT-PCR products of CHK/01/06 and CHK/03/06 virus isolates amplified with gene specific primers for the CHIK virus.
Lane 1—CHK/01/06 amplified with CHK SP FP1 and CHK SP RP5; ~550 bp
Lane 2—CHK/03/06 amplified with CHK SP FP1 and CHK SP RP5; ~550 bp
M—Molecular size marker; 1 kb ladder; (N3232S; New England Biolabs)
Lane 4—CHK/01/06 amplified with CHK SP FP3 and CHK SP RP4; ~686 bp
Lane 5—CHK/03/06 amplified with CHK SP FP3 and CHK SP RP4; ~686 bp Lane 6—CHK/01/06 amplified with CHK SP FP1 and CHK SP RP 5; ~637 bp Lane 7—CHK/03/06 amplified with CHK SP FP1 and CHK SP RP 5; ~637 bp FIG. 6 Haemagglutination (HA) of the CHK/03/06 virus using fresh goose erythrocytes. The first two rows is the HA titer of the virus harvest from Vero cells in serial dilution. The last two rows is the HA titer of the serially diluted purified CHIK virus preparation showing an increase in the HA titer.

Electron microscopy of the virus: The Transmission Electron microscopy (Hitachi H-7500) of the CHIK virus after ultracentrifugation was carried out by negative staining method using 2% uranyl acetate is depicted in FIG. 4.

EXAMPLE 7

Figure 5:
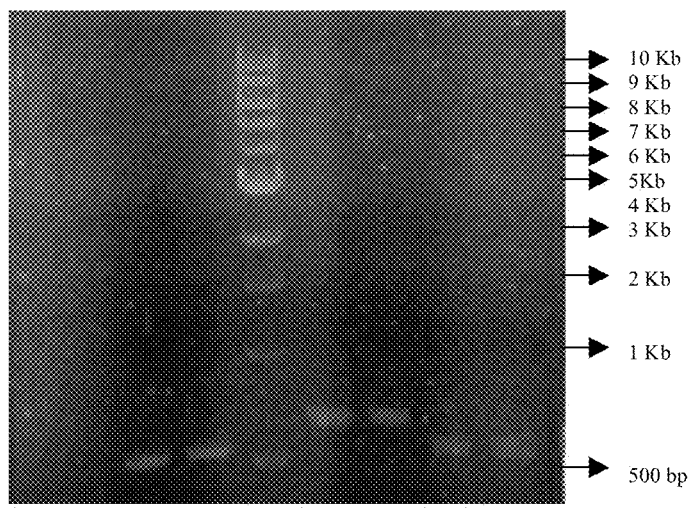

The genetic identity of the CHK/01/06 and CHK/03/06 Chikungunya virus isolates grown in Vero cells was confirmed by Reverse-Transcription-Polymerase Chain Reaction (RT-PCR) of the viral genomic RNA of the CHIK virus isolates. The virus genomic RNA was extracted from the virus culture in Vero cells using standard protocols. The total RNA was reverse transcribed in different reactions using oligodT (18 mer) and by primers specific for Chikungunya virus sequences. Alternatively, the PCR was carried out on the reverse transcribed product using gene specific forward and reverse primers as given below. The PCR was carried out using Vent DNA polymerase (New England Biolabs). A few examples of the RT-PCR of the cDNA of CHIK virus isolates are depicted in FIG. 5. The sequence of few of the forward primers and reverse primers used in the some of the PCR reactions are as follows:

```
SEQ ID NO. 11:
CHK SP FP1:      5' CTAAATAGGTACGCACTACAGC 3';

SEQ ID NO. 12:
CHK SP FP2:      5' TGGACTCCGCGCCCTACTATC 3';

SEQ ID NO. 13:
CHK SP FP3:      5' TACTCAGGAGGCCGGTTCAC 3';

SEQ ID NO. 14:
CHK SP RP4:      5' GTGTCCCATTGTTCCAG 3'; and,

SEQ ID NO. 15:
CHK SP RP5:      5' GTGAACCGGCCTCCTGAGTA 3'.
```

The RT-PCR amplified cDNA fragments were sequenced by dideoxy chain termination method. The deduced protein sequences were determined using universal genetic codes. Additional regions of the Chikungunya virus genome sequences were amplified with other gene specific primers, and sequences of the amplified DNA were determined by dideoxy chain termination method. The sequence of the RT-PCR products confirmed the identity of the Chikungunya virus isolates.

EXAMPLE 8

Heat Inactivation of the Virus:
The purified virions of CHK/03/06 isolates were heat inactivated at temperatures ranging from 50° C.-60° C. for 30-60 min. The infectivity of the virions was checked by re-infection of the Vero cells. No re-infection was observed.

EXAMPLE 9

Chemical Inactivation of the Virus:
The purified virions of CHIC/03/06 isolate were inactivated by chemical methods that includes but is not limited to one of the following methods: inactivation at concentrations ranging from 0.01% to 0.5% formalin (formaldehyde) for 2 hours at 37° C. followed by incubation at 4° C. for a period of 48-96 hours. The virions inactivated at the various concentrations of formalin were found to be non-infectious when re-infected in Vero cells after at least three serial passages. In an alternative inactivation method, the purified virions were inactivated with beta-propiolactone (BPL) at various concentrations ranging from 1:500 to 1:3000 of the BPL:virus and for two hours at 37 DEG C, followed by incubation at varying time intervals of 48-200 hours at 4° C. No re-infection of the virus was observed after three serial passages of the virus at a ratio of BPL:virus at 1:500 dilution to 1:1000 dilution. Inactivation of the virus could also be successfully carried out 22 DEG C for varying number of hours ranging from 48-96 hrs. No infectivity was observed with the formalin and beta-propiolactone inactivated virions at the range of concentrations and for the various time periods tested.

EXAMPLE 10

Measurement of the virus infectious titer: The virus infection titer of CHK/03/06 isolate was counted in PFUs (plaqueforming units/ml) by a plaque-counting method using Vero cells and by determining the TCID$_{50}$ (Tissue culture infectious dose) by standard protocols. The plaques could be ready by 36-48 hours and the titers could be determined by 30-48 hours. In Vero cells, various passages of the Vero-adapted virus yielded titers ranging upto $10^{8.5}$ TCID$_{50}$ An increase in titer was observed after passaging the virus through 2-day old mouse brain. The virus was plaque purified from passage 2 sample in Vero cells.

EXAMPLE 11

Determination of the Immunogenicity of the Virus:

An amount of the Chikungunya virus antigen of the CHK/03/06 isolate was measured by protein estimation by BCA method and by ELISA using rabbit anti-Chikungunya virus antisera. Polyclonal antibodies were raised in rabbit by injecting 100 μg of the purified Chikungunya virus CHK/03/06 isolate intradermally/subcutaneously/intramuscularly and injecting a similar amount of antigen as a booster dose 7-14 days after the first antigen administration. Injection of a single dose of virus purified from BHK21 cells gave an ELISA titer of ~6400, and a titer of >80 by virus neutralization assay compared to normal rabbit serum of ~4. Four samples of convalescent human antisera gave a varying titer of 80-240 as against control human serum that gave a titer of ~4. Antisera was also raised against both the CHK/01/06 and CHK/03/06 isolates of the virus. Good seroconversion was observed as determined by ELISA and by in vitro neutralization assay. The neutralizing assay titer observed after single booster injection was higher.

EXAMPLE 12

Figure 6:
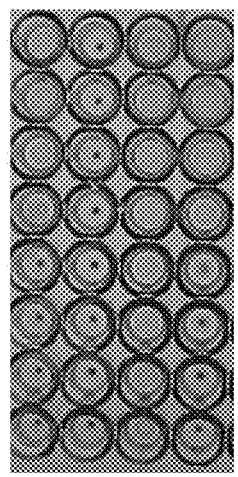
Figure 7:
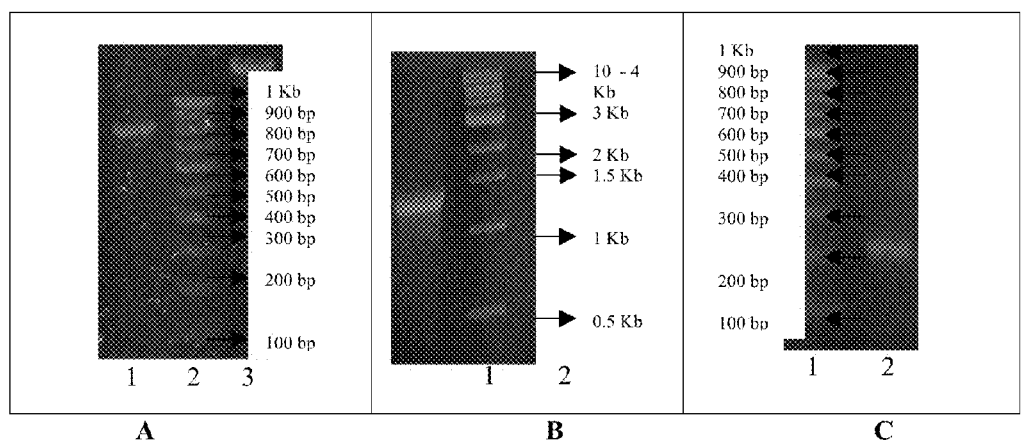
FIG. 7. RT-PCR of the viral structural proteins.

Haemagglutination and Haemagglutination Inhibition:

The hemagglutination titer was estimated by standard procedure using goose red blood cell suspension. Haemagglutination inhibition of the immune sera from rabbit and convalescent human sera were determined by standard protocols. Both the rabbit antisera and convalescent human sera showed haemagglutination inhibition. The HA titer of the purified virus was higher than the harvested neat virus sample. The HA titer of infected virus sample and the purified virus sample after serial dilutions are depicted in FIG. 6

EXAMPLE 13

Animal Testing:

Fifteen one month old Balb/c mice were used in each group. The animals in each group were injected intraperitoneally with about 0.2 ml to 0.5 ml/mouse of serially diluted vaccine preparation of the CHK/03/06 isolate ranging in dose from 1 μg to about 200 μgfor the different test groups. The animals were boosted 14 days after the first immunization. Blood was collected either at 7 and 14 days after the booster injection. Equal amount of serum was pooled for each group and complement was inactivated at 56° C. for about 30 min. The resultant serum was used for neutralizing test as an immune serum and for estimation of antibody titer by ELISA. In an alternate experiment, similar amount of the inactivated virus preparation was administered intramuscularly. The antibody response was higher with intramuscular injection. All the formulations contained the viral antigen along with aluminium hydroxide in 40 mM phosphate buffer, pH 6.8-7.2 containing 150 mM NaCl, 50 μg/dose oligonucleotides and varying amounts of excipients as mentioned in the Example below.

EXAMPLE 14

Formulation:

The formulation of Chikungunya virus antigen CHK/03/06 was prepared in 40 mM phosphate buffer, pH 6.9-7.2 with or without 154 mM NaCl. The viral preparations were formulated in a liquid formulation with aluminium hydroxide/aluminium phosphate containing either one or combination of sugars such as sucrose, maltose, trehalose, lactose, glucose, mannitol or sorbitol. The presence of sugars in the range of 0.5%-10% and preferably in the range of 0.5% to 5% conferred good stability on the formulation as determined by accelerated stability at 37 DEG C for three weeks. A significantly high titer of antibody response was obtained when oligonucleotides at a dose of 50 μg/dose was included in the liquid formulation. Similar formulation was also tested with phosphate-citrate buffer of pH 6.8-7.2 and no difference was observed. Higher concentration of above sugars, buffer and salt as upto 60% of the total solids conferred good stability on lyophilized formulation of the vaccine. The stability of the formulation was tested by potency tests in mice.

EXAMPLE 15 vRecombinant Cloning and Expression of the Viral Antigens in Prokaryotic and Eukaryotic Expression Systems:

The CHK/03/06 virus isolate was used as the source for cloning and expression of all viral antigens with the sequences given in SEQ ID NO. 1 to SEQ ID NO. 10. The complete open reading frame of the Chikungunya virus Structural polyprotein encoded by the SEQ ID NO.1 was amplified by RT-PCR of the viral genomic RNA using the primers CHKCPFP as the forward primer and CHKE1RP as the reverse primer to obtain a ~3776 bp PCR fragment. The PCR fragment was digested with Nde1 and BamH1 and cloned into the Nde1 and BamH1 sites of the prokaryotic expression vector, pET11B and the recombinant plasmid containing the insert was transformed in *E. coli* DH5a. In an alternative method, the open reading frame encoding the Chikungunya virus structural polyprotein, the SEQ ID NO.2 was cloned and expressed in a similar manner using CHKCKOZAKFP as the forward primer and CHKE1RP2 as the reverse primer to obtain a fragment of similar size. The SEQ ID NO. 2 has been amplified with a primer sequence that introduces a Kozak's consensus sequence at the 5' end for enhanced expression in eukaryotic expression system. The primer sequence CHKCKOZAKFP has EcoR1 site and CHKE1RP2 has a HindIII and Not1 sites to facilitate cloning into baculovirus vector pFastBac (Invitrogen Corporation, Carlsbad, USA) and *Pichia* vector pPIC3.5K (Invitrogen Corporation, Carlsbad, USA) respectively.

The SEQ ID NO. 2 was further amplified with a C-terminal primer that introduced 6-Histidine residues at the C-terminal end to obtain SEQ ID NO. 3.

SEQ ID NO.1 and SEQ ID NO.2 encode the protein of SEQ ID NO.4. SEQ ID NO. 3 encodes the protein of SEQ ID NO.5 that has the 6 His residues at the C-terminal end. The 6-Histidine residues at the C-terminal end of SEQ ID NO. 5, facilitates the purification of the expressed protein on Ni$^+$ affinity column. Both SEQ ID No.4 and SEQ ID NO.5 have been expressed for assembly of the virus like particle in yeast and in baculovirus mediated expression in Sf9 cells The PCR gene fragments corresponding to SEQ ID NO.2, and SEQ ID NO.3 were digested with EcoR1 and Not 1 and gel purified by standard protocols and cloned into EcoR1 and Not1 sites of the yeast expression vector pPIC3.5K (Invitrogen Corporation, Carlsbad, USA). The positive clones were selected after confirmation by PCR using the same primers. The recombinant plasmid encoding the complete structural protein of SEQ ID NO.4 and SEQ ID NO.5 was transformed into *Pichia Pastoris* GS 115 as per the manufacturers (Invitrogen) instruction and as outlined in their protocols. The PCR amplified fragment has been cloned into the AOX1 locus and expressed under the AOX1 promoter by methanol induction. The cloning, screening, isolation of the recombinant *Pichia* strains and induction of the cloned gene with methanol were carried out as per the User's manual "A Manual of Methods for Expression of Recombinant Proteins in *Pichia pastoris*" Version M January 2002, of *Pichia* Expression Kit, Catalog #K1710-01, Invitrogen Corporation, Carlsbad, USA).

The complete Open Reading Frame (ORF) of the Chikungunya virus Structural polyprotein encoded by the SEQ ID NO.2 and SEQ ID NO.3 amplified by RT-PCR were digested with EcoR1 and Hind III, gel purified and cloned into the EcoR1 and Hind III sites of the pFastBac vector under the control of the polyhedron promoter (Invitrogen Corporation, Carlsbad, USA). The Methods for cloning and selection of the recombinant baculovirus vector as are exactly outlined in the User's manual of Bac to Bac Baculovirus expression system ("An efficient site-specific transposition system to generate baculovirus for high-level expression of recombinant proteins" Version D, 6 April 2004, Invitrogen Corporation, Carlsbad, USA). In brief, the method utilizes a site specific transposition of the expression cassette such as the recombinant pFastBac vector with the cloned inserts as described above into a baculovirus shuttle vector (bacmid) propagated in *E. coli*. Recombinant pFastBac vector containing one of the inserts SEQ ID NO.4 or SEQ ID NO.5 cloned under the control of the polyhedron promoter is transformed into competent cells of *E. coli* Max Efficiency DH10Bac™, that contains a baculovirus shuttle vector (bMON 14272) and a helper plasmid (pMON7124) that facilitates transposition to allow efficient re-generation of the recombinant bacmid following the transposition of the pFastBac recombinant constructs containing the SEQ ID NO. 4 or SEQ ID NO. 5. The recombinant bacmid were selected on ampicillin, gentamicin and kanamycin containing plates by blue/white selection using bluo-gal and IPTG. The recombinant bacmid was isolated by standard protocols similar to that of isolation of plasmid DNA and 1 μg of the bacmid DNA was used for transfection with the use of Cellfectin™ reagent into Sf9 insect cells that were grown in Grace's insect cell medium (Invitrogen Corporation, USA). The methods used for transfection, isolation and titration of P1 viral stock are exactly as described in the User's manual of Bac-to-Bac Baculovirus Expression system as given above. The open reading frame of each of the structural antigens such as the Capsid, E3, E2, 6K polypeptide and E1 structural proteins corresponding to the following sequence IDs: SEQ ID NO.6, SEQ ID NO.7, SEQ ID NO.8, SEQ ID NO.9 and SEQ ID NO. 10 respectively encoded in the structural polyprotein sequence were amplified by PCR using gene specific primers as outlined below in the first step of amplification. In the second step reverse primers that encode for 6 histidine residues were used for PCR (primer sequences not given) of each of the individual genes and cloned into pET11 B for prokaryotic expression in *E. coli* and in pFastBac vector for baculovirus mediated expression in insect cells.

Some of the PCR primers originally designed for *E. coli* and baculovirus cloning did not have suitable restriction sites for cloning into pPIC3.5 K for expression in *Pichia pastoris*, Those PCR fragments that had EcoR1 site at the 5' end and BamH1 site in the C-terminal by virtue of the presence of these restriction sites in the forward and reverse primers respectively, were initially cloned into the EcoR1 and BamH1 sites of the vector pBluescript SK+. The selected recombinant clone was digested with EcoR1 and Not1 and the digested fragment was then subcloned in pPIC3.5K for yeast transformation as described above. The primer sequences used for various amplifications are as indicated below. Expression of E1 antigens in *E. coli* and the Capsid protein in yeast is shown in FIG. 8 and in FIG. 9.

```
Primer sequences:
SEQ ID NO. 16:
CHKCKOZAKFP:
5' ATTGAATTCACCATGGAGTTCATCCCAACCCAAAC 3'

SEQ ID NO. 17:
CHKE1RP2:
5' AACAAGCTTGCGGCCGCTTAGTGCCTGCTGAACGACACG 3'

SEQ ID NO. 18:
CHKSPE3FP:
5' ACCGAATTCATATGAGTCTTGCCATCCCAGTTATG 3'

SEQ ID NO. 19:
CHKSPE3RP:
5' TGCAAGCTTGGATCCTTAGCGTCGCTGGCGGTGGGGAG 3'

SEQ ID NO. 20:
CHKSP6KFP:
5' ACGGAATTCATATGGCCACATACCAAGAGGCTGCG 3'

SEQ ID NO. 21:
CHKSP6KRP:
5' ATTAAGCTTGGATCCTTAGGTGCCCACACTGTGAGCGC 3'

SEQ ID NO. 22:
CHKCPFP:
5' ACAGAATTCATATGGAGTTCATCCCAACCCAAAC 3'

SEQ ID NO. 23:
CHKCPRP:
5' ATTAAGCTTGGATCCTTACCACTCTTCGGCCCCCTCGGGG 3'

SEQ ID NO. 24:
CHKE1FP:
5' TAGAATTCATATGTACGAACACGTAACAGTGATCC 3'

SEQ ID NO. 25:
CHKE1RP:
5' TATAAGCTTGGATCCTTAGTGCCTGCTGAACGACACGC 3'

SEQ ID NO. 26:
CHKE2FP:
5' TCGGAATTCATATGAGCACCAAGGACAACTTCAATGTC 3'

SEQ ID NO. 27:
CHKE2RP:
5' TCCAAGCTTGGATCCTTACGCTTTAGCTGTTCTGATGCAGC 3'
```

EXAMPLE 16

The recombinant antigens expressed in either prokaryotic or eukaryotic expression system can be used for diagnostic purpose such as in ELISA. ELISA has been established using the inactivated whole virus and using rabbit antisera. Similar technique can be established using the purifed recombinant antigens instead of the whole virus as antigen. Polyclonal antisera or monoclonal antibody against the virus antigens particularly the structural antigens can be used as immunotherapeutic agent.

Bibliography
1. Banerjee K and Ranadive S N. 1988. Oligonucleotide fingerprinting of Chikungunya virus strains. Ind. J. Med. Res. 87:531-541.
2. Bedekar S D and Pavri K M. 1969a. Studies with Chikungunya virus. Part I. Susceptibility of birds and small mammals. Ind. J. Med. Res. 57:1181-1192.

3. Bedekar S D and Pavri K M. 1969b. Studies with Chikungunya virus. Part II. Serologiacl survey of humans and animals in India. Ind. J. Med. Res. 57:1193-1197.
4. Casals J. 1957. The arthropod-borne group of animal viruses. Trans. N.Y. Acad. Sci. 19:219-235.
5. Chain M M T, Doane R W and McLean D M. 1966. Morphological development of Chikungunya virus. Can. J. Microbiol. 12:895-899.
6. Chakravarthy S K and Sarkar J K. 1969. Susceptibility of new born and adult laboratory animals to Chikungunya virus. Ind. J. Med. Res. 57:1157-1164.
7. Chaturvedi U C, Mehrotra N K, Mathur A, Kapoor A K and Mehrotra R M. 1970. Chikungunya virus HI antibodies in the population of Lucknow and Kanpur. Ind. Jour. Med. Res. 58:297-301.
8. Eckels K H, Harrison V R and Hetrick F M. 1970. Chikungunya virus vaccine prepared by Tween-ether extraction. Applied Microbiol. 19:321-325.
9. Edelman R, Tacket C O, Wasserman S S, Bodison S A, Perry J G and Magniafico J A. 2000. Phase II safety and immunogenicity study of live chikungunya virus vaccine TSI-GSD-218. Am. J. Trop. Med. Hyg. 62:681-685.
10. Fauquet C M, Mayo M A, Maniloff J, Desselberger J and Ball L A (Eds.). 2005. 8th Report of the International Committee on Taxonomy of Viruses.
11. Giovarelli M, Viano I, Zucca M, Valbonesi R and Dianzani F. 1977. Effect of anti-□-chain-specific immunosuppression on Chikungunya virus encephalitis of mice. Infect. Immun. 16:849-852.
12. Hahon N and Hankins W A. 1970. Assay for Chikungunya virus in cell monolayers by immunofluorescence. Applied Microbiol. 19:224-231.
13. Hahon N and Zimmerman W D. 1970. Chikungunya virus infection of cell monolayers by cell-to-cell and extracellular transmission. Applied Microbiol. 19:389-391.
14. Hannoun. 1968. Arbovirus haemgglutinins: differential susceptibility to trypsin. Nature 219:753-755.
15. Harrison V R, Binn L N and Randall R. 1967. Comparative immunogenicities of chikungunya vaccines prepared in avian and mammalian tissues. Amer. J. Trop. Med. Hyg. 16:786-791.
16. Harrison V R, Eckels K H, Bartelloni P J and Hampton C. 1971. Production and evaluation of a formalin-killed chikungunya vaccine. J. Immunol. 107:643-647.
17. Hearn H J and Rainey C T. 1963. Cross-protection in aminals infected with group A arboviruses. J. Immunol. 90:720-724.
18. Heise M T, Simpson D A and Johnston J E. 2000. Sindbis-group alphavirus replication in periosteum and endosteum of long bones in adult mice. J. Virol. 74:9294-9299.
19. Higashi N, Matsumoto A, Tabata K and Nagatomo Y. 1967. Electron microscope study of development of Chikungunya virus in green monkey kidney stable (Vero) cells. Virology 33:55-69.
20. Khan A H, Morita K, Parquet M C, Hasebe F, Mathenge E G M and Igarashi A. 2002. Complete nucleotide sequence of chikungunya virus and evidence for an internal polyadenylation site. J. Gen. Virol. 83:3075-3084.
21. Killington R A, Stokes A and Hierholzer J C. 1996. Virus purification. In "Virology methods manual," Mahy B W J and Kangro (Eds). Academic Press, San Diego, Calif., pp 71-89.
22. Klien F, Mahlandt B G, Cockey R R and Lincoln R E. 1970. Concentration of Rift valley fever and Chikungunya viruses by precipitation. Applied Microbiol. 20:346-350.
23. Lanciotti R S, Ludwig M L, Rwaguma E B, Lutwama J J, Kram T M et al. 1998. Emergence of epidemic O' nyong-nyong fever in Uganda after a 35-year absence: genetic characterization of the virus. Virology 252:252-268.
24. Levitt N H, Ramsburg H H, Hasty S E, Repik P M, Cole F E Jr and Lupton H W. 1986. Development of an attenuated strain of chikungunya virus for use in vaccine production. Vaccine 4:157-162.
25. McClain D J, Pittman P R, Ramsburg H H, Nelson G O, Rossi C A, Mangiafico J A, Schmaljohn A L and Malinoski F J. 1998. Immunologic interference from sequential administration of live attenuated alphavirus vaccines. J. Infect. Dis. 177:634-641.
26. McIntosh B M, Paterson H E, McGillivray G and DeSousa J. Further studies on the Chikungunya outbreak in Southern Rhodesia in 1962.1. Mosquitoes, wild primates and birds in relation to the epidemic. Ann. Trop. Med. Parasitol. 58:45-51.
27. Myers R M, Carey D E, Reuben R, Jesudass E S, De Ranitz C, Jadhav M. 1965. The 1964 epidemic of Dengue-like fever in South India: isolation of Chikungunya virus from human sera and from mosquitoes. Ind. J. Med. Res. 53:694-701.
28. Nimmannitya S, Halstead S B, Cohen S N and Margiotta M R. 1969. Dengue and chikungunya virus infection in man in Thailand, 1962-1964.1. Observations on hospitalized patients with hemorrhagic fever. Am. J. Trop. Med. Hyg. 18:954-971.
29. Parks J J and Price W J. 1958. Studies on immunologic overlap among certain arthropod-borne viruses. Am. J. Trop. Med. Hyg. 67:187-206.
30. Paul S D and Singh K R P. 1968. Experimental infection of Macaca radiata with Chikungunya virus and transmission of virus by mosquitoes. Ind. J. Med. Res. 56:802-810.
31. Porterfield J S. 1961. Cross-neutralization studies with group A arthropod-borne viruses. Bull WHO 24:735-741.
32. Powers A M, Brault A C, Tesh R B and Weaver S C. 2000. Re-emergence of chikungunya and o'nyong-nyong viruses: evidence for distinct geographical lineages and distant evolutionary relationships. J. Gen. Virol. 81:471-479.
33. Ranadive S N and Banerjee K. 1990. Cloning and expression of Chikungunya virus genes coding structural proteins in *Escherichia coli*. Ind. J. Med. Res. 91:386-392.
34. Rao T R, Carey D E and Pavri K M. 1965. Preliminary isolation and identification of Chikungunya virus from cases of Dengue-like illness in Madras city. Ind. J. Med. Res. 53:689-693.
35. Ravi V. 2006. Re-emergence of chikungunya virus in India. Ind. J. Med. Microbiol. 24:83-84.
36. Sarkar J K, Chatterjee S N and Chakravarty S K. 1964. Haemorrhagic fever in Calcutta: some epidemiological observations. Ind. J. Med. Res. 52:651-659.
37. Sarkar J K, Chatterjee J K, Chakravarti S K and Mitra A C. 1965. Chikungunya virus infection with haemorrhagic manifestations. Ind. Jour. Med. Res. 53:921-925.
38. Schuffenecker I, Iteman I, Michault A, Murri S, Frangeul L, Vaney M-C, Lavenir R, Pardigon N, Reynes, J-M, Pettinelli F, Biscornet L, Diancourt L, Michel S, Duquerroy S, Guigon G, Frenkiel M-P, Brehin A-C, Cubito N, Despres P, Kunst F, Rey F A, Zeller H and Brisse S. 2006. Genome microevolution of Chikungunya viruses causing the Indian Ocean outbreak. PLOS Med. 3:e263.

39. Shaw K V, Clarence J G, Jr., and Banerjee G. 1964. Virological investigation of the epidemic of haemorrhagic fever in Calcutta: isolation of three strains of Chikungunya virus. Ind. J. Med. Res. 52:676-682.
40. Simizu B, Yamamoto K, Hashimoto K and Ogata T. 1984. Structural proteins of Chikungunya virus. J. Virol. 51:254-258.
41. Umrigar M D and Kadam S S. 1974. Comparative sensitivity of suckling mice and Vero cells for primary isolation of Chikungunya virus. Ind. J. Med. Res. 62:1893-1895.
42. Weiss H J, Halstead S B and Russ S B. 1965. Hemorrhagic disease in rodents caused by Chikungunya virus. 1. Studies of hemostasis. Proc. Soc. Exp. Biol. Med. 119:427-432.

We Claim:

1. An immunogenic composition comprising an isolated Chikungunya virus antigen selected from SEQ ID NO: 5 to SEQ ID NO: 10.

2. The immunogenic composition according to claim 1, wherein the Chikungunya virus antigen is purified.

3. The immunogenic composition according to claim 1, wherein the Chikungunya virus antigen comprises the immunogenic amino acid sequence consisting of SEQ ID No. 5.

4. The immunogenic composition according to claim 1, wherein the Chikungunya virus antigen is selected from the group consisting of SEQ ID NO: 6 to SEQ ID NO: 10.

5. The immunogenic composition according to claim 1, further comprising a physiologically acceptable buffer selected from at least one buffer of the group consisting of: phosphate buffer and phosphate-citrate buffer, and further comprising an adjuvant selected from the group consisting of the following: aluminium hydroxide and aluminium phosphate.

6. The immunogenic composition according to claim 1, wherein the immunogenic composition is capable of being administered by at least one route of administration selected from; intramuscular, intradermal, subcutaneous, intravenous, oral and intranasal.

7. An immunogenic composition comprising at least one antigen of claim 1 in a pharmacologically and physiologically acceptable carrier with or without an adjuvant and a stabilizing agent, wherein the immunogenic composition is capable of eliciting an immune response against Chikungunya virus.

8. The immunogenic composition according to claim 7, wherein the adjuvant is at least one adjuvant selected from the group consisting of the following: aluminium hydroxide and aluminium phosphate.

9. An isolated Chikungunya virus antigen, wherein the Chikungunya virus antigen comprises any one of SEQ ID NO: 5 through SEQ ID NO: 10 and is used for diagnosing Chikungunya virus infections in mammals.

10. A recombinant expression plasmid comprising a Chikungunya virus antigen encoding DNA sequence selected from the group consisting of: SEQ ID NO: 1, SEQ ID NO: 2 and SEQ ID NO: 3.

11. The recombinant expression plasmid according to claim 10, wherein the nucleotide sequences of SEQ ID NO: 1, SEQ ID NO: 2 or SEQ ID NO: 3 have been modified to include a Kozak's consensus sequence for enhanced eukaryotic expression.

12. The recombinant expression plasmid according to claim 10, wherein the plasmid is a prokaryotic expression plasmid.

13. The recombinant expression plasmid according to claim 10, wherein the plasmid is a eukaryotic expression plasmid.

14. A method of expressing Chikungunya virus like particles, comprising the steps of:
   i) introducing the recombinant expression plasmid of claim 10 into isolated host cells;
   ii) culturing the host cells of step i);
   iii) harvesting the cells following step ii) and isolating Chikungunya virus like particles therefrom; and
   iv) purifying the virus like particles by at least one of the following methods: ion exchange chromatography, gel filtration, affinity chromatography, hydrophobic column chromatography, fractionation with salt, centrifugation, and electrophoresis.

\* \* \* \* \*